(12) United States Patent
Engles et al.

(10) Patent No.: US 12,016,817 B2
(45) Date of Patent: *Jun. 25, 2024

(54) LOW ENERGY ACOUSTIC PULSE APPARATUS AND METHOD

(71) Applicant: Acoustic Wave Cell Therapy, Inc., Van Nuys, CA (US)

(72) Inventors: Charles R. Engles, Portola Valley, CA (US); Yung Chen Su, Taoyuan (TW)

(73) Assignee: Acoustic Wave Cell Therapy, Inc., Van Nuys, CA (US)

(*) Notice: Subject to any disclaimer, the term of this patent is extended or adjusted under 35 U.S.C. 154(b) by 1076 days.

This patent is subject to a terminal disclaimer.

(21) Appl. No.: 16/665,855

(22) Filed: Oct. 28, 2019

(65) Prior Publication Data
US 2020/0054519 A1 Feb. 20, 2020

Related U.S. Application Data

(63) Continuation of application No. 16/135,863, filed on Sep. 19, 2018, now Pat. No. 10,500,128, which is a
(Continued)

(51) Int. Cl.
*A61H 23/00* (2006.01)
*A61B 17/00* (2006.01)
(Continued)

(52) U.S. Cl.
CPC .......... *A61H 23/008* (2013.01); *A61H 19/44* (2013.01); *A61H 21/00* (2013.01); *A61H 23/006* (2013.01);
(Continued)

(58) Field of Classification Search
CPC ...... A61H 23/008; A61H 21/00; A61H 19/44; A61H 23/0236; A61H 23/006;
(Continued)

(56) References Cited

U.S. PATENT DOCUMENTS 7,311,678 B2 12/2007 Spector
7,601,127 B2 10/2009 Schultheiss et al.
(Continued)

OTHER PUBLICATIONS

Azhari, Basics of Biomedical Ultrasound for Engineers, John Wiley & Sons, Inc., 2010, pp. 313-314.
(Continued)

*Primary Examiner* — Thaddeus B Cox
*Assistant Examiner* — Joshua Daryl D Lannu
(74) *Attorney, Agent, or Firm* — Law Office of Alan W. Cannon

(57) ABSTRACT

An apparatus for generating an acoustic energy pulse and delivering it into a body is described. The apparatus includes a generator for creating an acoustic energy pulse having an energy density field that can be measured at all points within a space in the shape of an imaginary cylinder having a length greater than or equal to 2 cm and a diameter. The cylindrically shaped space has a cylinder longitudinal axis oriented relative to a longitudinal axis of the energy pulse at an angle in the range from zero to twenty degrees. A minimum energy density for the pulse at all locations within the cylindrically shaped space is at least 50% of a maximum energy density for the pulse within the space.

49 Claims, 26 Drawing Sheets

Related U.S. Application Data continuation-in-part of application No. 15/928,490, filed on Mar. 22, 2018, now abandoned.

(51) Int. Cl.

| | | |
|---|---|---|
| *A61B 17/22* | (2006.01) | |
| *A61B 17/225* | (2006.01) | |
| *A61B 18/00* | (2006.01) | |
| *A61F 7/00* | (2006.01) | |
| *A61H 19/00* | (2006.01) | |
| *A61H 21/00* | (2006.01) | |
| *A61H 23/02* | (2006.01) | |
| *A61N 7/00* | (2006.01) | |
| *G10K 15/04* | (2006.01) | |

(52) U.S. Cl.
CPC ............... *A61H 23/0236* (2013.01); *A61B 2017/00805* (2013.01); *A61B 2018/00523* (2013.01); *A61F 2007/005* (2013.01); *A61H 2201/0119* (2013.01); *A61H 2201/1238* (2013.01); *A61H 2201/1654* (2013.01)

(58) Field of Classification Search
CPC .... A61H 2201/0119; A61H 2201/1238; A61H 2201/1654; A61B 2017/00805; A61B 2018/00523; A61B 17/22004; A61B 17/2251; A61F 2007/005; G10K 15/043; A61N 7/00
See application file for complete search history.

(56) References Cited

U.S. PATENT DOCUMENTS

| | | | |
|---|---|---|---|
| 7,610,079 B2 | 10/2009 | Schwarze et al. | |
| 7,695,443 B2 | 4/2010 | Voss | |
| 7,775,995 B2 | 8/2010 | Voss | |
| 7,867,178 B2 | 1/2011 | Simnacher | |
| 8,257,282 B2 | 9/2012 | Uebelacker et al. | |
| 8,529,451 B2 | 9/2013 | Warlick et al. | |
| 8,535,249 B2 | 9/2013 | Uebelacker et al. | |
| 8,900,166 B2 | 12/2014 | Spector | |
| 9,161,768 B2 | 10/2015 | Cioanta et al. | |
| 9,456,835 B2 | 10/2016 | Zhong et al. | |
| 10,500,128 B2 * | 12/2019 | Engles | A61H 23/0236 |
| 2005/0038362 A1 | 2/2005 | Schultheiss | |
| 2006/0004306 A1 | 1/2006 | Altshuler et al. | |
| 2007/0167883 A1 | 7/2007 | Voss | |
| 2012/0239055 A1 * | 9/2012 | Spector | A61B 17/225 |
| | | | 606/119 |
| 2014/0088465 A1 | 3/2014 | Cioanta et al. | |
| 2014/0330174 A1 * | 11/2014 | Warlick | A61N 7/00 |
| | | | 601/2 |
| 2015/0224345 A1 * | 8/2015 | Warlick | A61N 7/00 |
| | | | 601/2 |
| 2016/0310766 A1 | 10/2016 | Cioanta | |
| 2017/0246481 A1 * | 8/2017 | Mishelevich | A61N 2/006 |
| 2017/0258676 A1 | 9/2017 | Lue et al. | |

OTHER PUBLICATIONS

Direx, LSWT—Clinical Data and Reports, International Journal of Impotence Research, 2014, p. 36.
MTS Shockwave & Lithotripsy, Applicator information, MTS Europe GmbH, 2009, pp. 1-12.
Ogden et al., Principles of Shock Wave Therapy, Clinical Orthopaedics and Related Research, No. 387, pp. 8-17, 2001.
International Search Report of PCT/US2018/051744 dated Feb. 12, 2019.

* cited by examiner

LOW ENERGY ACOUSTIC PULSE APPARATUS AND METHOD

CROSS-REFERENCE

This application is a continuation of application Ser. No. 16/135,863, filed Sep. 18, 2018, now U.S. Pat. No. 10,500,128, which is a continuation-in-part application of U.S. application Ser. No. 15/928,490, filed Mar. 22, 2018, both of which applications and which patent are hereby incorporated herein, in their entireties, by reference thereto and to which applications we claim priority under 35 USC § 120.

FIELD OF THE INVENTION

The present invention relates to the field of low energy acoustic pulse (LEAP) therapy. More particularly the present invention relates to treatment of the urinary system using LEAP therapy, even more particularly to treatment of the female urethra.

BACKGROUND OF THE INVENTION

An established form of acoustic pulse therapy, extracorporeal shockwave therapy, is used in physical therapy, orthopedics, urology and cardiology. The shockwaves are abrupt, high amplitude pulses of mechanical energy, similar to sound waves. Shockwaves were originally used in medicine for breaking up kidney stones using a procedure known as lithotripsy. This is a high intensity application of acoustic pulse therapy that is used to disrupt and destroy kidney stones.

LEAP therapy uses a much lower energy form of acoustic pulses than traditional shockwaves and can be applied for treatment of tissues, rather than to destroy them. Various forms of LEAP treatment devices are currently available, but there remains a continuing need for LEAP apparatus tailored to specific applications for which the therapy is being applied. In particular, LEAP apparatus are needed which can deliver a relatively uniform amount of acoustic pulse energy to the entire target tissue.

U.S. Patent Application Publication No. 2012/0239055 A1 to Spector et al. discloses a method for treating the female pelvic floor and perineal organs with extracorporeal shockwaves. Although treatment of urinary incontinence is mentioned in a long list of potential uses, there are no specific teachings for successfully completing such treatment. Further, in general, the shockwave generating device can be inserted through the vaginal canal to treat Urethral Syndrome. This exposes the vaginal canal to the extracorporeal shockwaves, which could result in damage thereto, or other unintended consequences, including, but not limited to pain. Still further, the shockwave device produces a focal zone and thereby applies shockwave energy at substantially different levels to different portions of the target tissue being treated. Also, being a focused device, the device of Spector et al would require applying shockwaves from multiple different positions along the length of the vaginal canal, as the wave width is only sufficient to apply to a small portion of the urethra from each application location within the vaginal canal. Because of inherent differences in the sizes and geometries of vaginal canals among various patients, there would also be a need to adjust the size of the probe of Spector et al. in order to accommodate fits to different sizes of vaginal canals. Patients with vaginal canals smaller than the minimum feasible size of the probe could not be treated at all.

U.S. Application Publication No. 2014/0330174 A1 to Warlick et al. discloses a method of treatment of vaginal tissue inflamed or damaged by complications from use of surgical mesh, which method includes emission of acoustic shock waves which can be convergent, divergent, planar or near planar. The devices of Warlick et al. use a parabolic reflector with an electrohydraulic device to provide divergent, planar or nearly planar wave patterns. However, the present inventors' observations have been that electrohydraulic devices with parabolic reflections do not produce planar waves. There is no specification by Warlick et al. as to the size or shape of an energy field produced by any of the embodiments shown, nor any teaching as to what a desired or appropriate energy field would look like. Further, if the target site is the vaginal tissue or organ subjected to a surgical procedure exposing at least some if not all of the tissue or organ within the body cavity the target site may be such that the patient or the generating source must be reoriented relative to the site and a second, third or more treatment dosage can be administered. Thus, because all of a significant volume of the target site cannot be captured by application of shockwaves from a single location, this complicates the procedure and also adds to the expense of the procedures required. It is also disclosed that a key advantage of the methodology of U.S. Application Publication No. 2014/0330174 A1 is that it is complementary to conventional medical procedures. There is no disclosure of treating female urinary incontinence by this method alone. The methods described are primarily directed to early prevention therapies to stimulate tissue or organ modeling to be maintained within acceptable ranges prior to an exposure to a degenerative condition occurring. This is disclosed to be valuable in the prevention of age related complications from later implantation of screen mesh for example. Shock waves can be emitted through the perineum tissue at the skin's surface and directed to the vaginal tissue or pelvic organs into the pelvic cavity. Alternatively, the shock waves can be administered via a vaginal probe that can emit spherical waves or planar waves. This vaginal probe simply can be directed into contact with the vaginal tissue to be treated. With either method the emitted waves are directed to the vaginal tissue or the pelvic organ. Treatment of the urethra along its length from either a vaginal or a perineal location would require multiple positions of the shockwave emitter, and a vaginal approach would suffer the same size drawbacks as noted above.

U.S. Pat. No. 9,161,768 to Cioanta et al. discloses extracorporeal shockwave devices with reversed applications. For example, a long reflector having an elongated shape and multiple discharge points is disclosed. The penetration depth to be achieved by the shockwave will dictate the depth of the reflector shape, which can be shallow for superficial applications or very deep for applications where the focus is deep inside the human body. In each case the shockwaves are focused and would not deliver a relatively uniform amount of energy to a target tissue.

Applicator information for DERMAGOLD 100® and ORTHOGOLD100® probes by MTS Shockwave Technology and Lithotripsy shows waveforms for probes that generate shockwaves by the electrohydraulic principle. Even those waveforms that are referred to as "unfocused" (e.g., OP155 waveforms shown on page 2 of the brochure) are focused to a degree, as illustrated by the red coloration in the center portion of the waveform that is surrounded by the yellow coloration in the remainder of the waveform. Because of the lack of uniformity of the waveforms, and the inability of the waveforms to achieve a sufficient width for a sufficient length at a sufficient power level, these devices are not sufficient to therapeutically treat the female urethra from a single treatment location, due to the diameter (including the urethral sphincter muscles) and length of the female urethra, which average about 16 mm and 4 cm, respectively. Although there are waveforms of the DERMAGOLD 100® apparatus that include 14 mm, 16 mm and greater focal diameters, these waveforms are not uniform, as they are more concentrated along the central axis of the waveform and the full width of the waveform does not extend over a length of 4 cm. These waveforms cannot effectively envelop the urethra and urethral sphincter muscles sufficiently for use in treating the female urethra. Furthermore, the energy flux density (EFD) levels required to achieve focal diameters of 15 mm-16 mm, i.e., 0.12-0.13 mJ/mm$^2$, are too high to be tolerated by a patient being treated in the area of the female urethra. As the EFD levels decrease, the focal diameters of the waveforms of the DERMAGOLD 100® apparatus also decrease, and thereby have even less ability to envelop the urethra and urethral sphincter muscles. There remains a need for improvement in energy level uniformity through an energy field over the space that encompasses the target tissue that therapy is being applied to.

There remains a need for improved apparatus that applies an appropriate energy level of LEAP to a target tissue and applies it more uniformly over the target tissue.

There remains a need for improved apparatus that applies desired amounts of energy via LEAP to a target tissue, while minimizing the amounts of energy applied to tissues adjacent to the target tissue.

There remains a need for improved apparatus that can achieve a therapeutic result from application of LEAPs from only one location, without the need to reposition the apparatus or patient and reapply LEAPs.

There remains a need for improved apparatus that can achieve a therapeutic result from application of LEAPs from only one location, along the length of the female urethra, to effectively treat female urinary incontinence, without the need to reposition the apparatus or patient and reapply LEAPs from a second or additional locations, and wherein the LEAPs applied are at a power level to produce a maximum energy flux density that is applied to the target tissue that is tolerable to the patient, so as not to produce intolerable pain or tissue damage.

There remains a need for apparatus that are more user friendly and easier for the user to operate, including performance of targeting and application of therapy.

SUMMARY OF THE INVENTION

The present invention provides apparatus and methods for generation and delivery of low energy acoustic pulses (LEAP). In one aspect of the present invention, an apparatus for generating an acoustic energy pulse includes: a generator for creating the acoustic energy pulse having an energy density field that can be measured at all points within a space in the shape of an imaginary cylinder having a length greater than or equal to 2 cm and a diameter; wherein the cylindrically shaped space has a proximal end, a distal end and a cylinder longitudinal axis, the cylinder longitudinal axis oriented relative to a longitudinal axis of the acoustic energy pulse at an angle in the range from zero to twenty degrees; the proximal end located at a first distance from the generator, the distal end located at a second distance from the generator, wherein the first distance is less than the second distance; and wherein a minimum energy density for the pulse at all locations within the cylindrically shaped space is at least 50% of a maximum energy density for the pulse within the space.

In at least one embodiment, the maximum energy density is in a range from 0.005 mJ/mm$^2$ to 0.025 mJ/mm$^2$, and the diameter is in a range from 10 mm to 18 mm.

In at least one embodiment, the maximum energy density is in a range from greater than 0.025 mJ/mm$^2$ to 0.04 mJ/mm$^2$, and the diameter is greater than 11 mm.

In at least one embodiment, the maximum energy density is in a range from greater than 0.04 mJ/mm$^2$ to 0.05 mJ/mm$^2$, and the diameter is greater than 12 mm.

In at least one embodiment, the maximum energy density is in a range from greater than 0.05 mJ/mm$^2$ to 0.08 mJ/mm$^2$, and the diameter is greater than 13 mm.

In at least one embodiment, the maximum energy density is in a range from 0.08 mJ/mm$^2$ to 0.11 mJ/mm$^2$, and the diameter is greater than 15 mm.

In at least one embodiment, the apparatus comprises a housing and at least a portion of the generator is contained within the housing, wherein the minimum dimension of the housing orthogonal to the longitudinal axis of the cylinder is less than or equal to 175 mm.

In at least one embodiment, the proximal end is located no more than 100 mm from a surface of the generator from which the acoustic energy pulse is delivered.

In at least one embodiment, the length of the cylinder is greater than or equal to 3 cm.

In at least one embodiment, the acoustic energy pulse comprises a divergent or planar acoustic pulse.

In at least one embodiment, the acoustic energy pulse is an acoustic shockwave pulse.

In at least one embodiment, the acoustic pulse is electromagnetically produced.

In at least one embodiment, the cylindrically shaped space is coaxial with a longitudinal axis of the acoustic energy pulse.

In another aspect of the present invention, a method of delivering an acoustic energy pulse includes: providing an acoustic energy pulse generating apparatus; generating an acoustic energy pulse and delivering the acoustic energy pulse from the acoustic energy pulse generating apparatus; wherein the acoustic energy pulse has an energy density field that can be measured at all points within a space in the shape of an imaginary cylinder having a length greater than or equal to 2 cm and a diameter; wherein the cylindrically shaped space has a proximal end, a distal end and a cylinder longitudinal axis, the cylinder longitudinal axis oriented relative to a longitudinal axis of the acoustic energy pulse at an angle in the range from zero to twenty degrees; the proximal end located at a first distance from the generating apparatus, the distal end located at a second distance from the generating apparatus, wherein the first distance is less than the second distance; and wherein a minimum energy density for the pulse at all locations within the cylindrically shaped space is at least 50% of a maximum energy density for the pulse within the space.

In at least one embodiment, the maximum energy density is in a range from 0.009 mJ/mm$^2$ to 0.044 mJ/mm$^2$, and the diameter is greater than 12 mm.

In at least one embodiment, the herein said maximum energy density is in a range from 0.009 mJ/mm$^2$ to 0.044 mJ/mm$^2$, and the diameter is in a range from 10 mm to 18 mm.

In at least one embodiment, the maximum energy density is in a range from greater than 0.044 mJ/mm$^2$ to 0.07 mJ/mm$^2$, and the diameter is greater than 13 mm.

In at least one embodiment, the maximum energy density is in a range from greater than 0.07 mJ/mm$^2$ to 0.088 mJ/mm$^2$, and the diameter is greater than 14 mm.

In at least one embodiment, the maximum energy density is in a range from greater than 0.088 mJ/mm$^2$ to 0.14 mJ/mm$^2$, and the diameter is greater than 17 mm.

In at least one embodiment, the acoustic energy pulse generating apparatus includes a housing at least partially surrounding an acoustic energy pulse generator, wherein a minimum dimension of the housing orthogonal to the longitudinal axis of the acoustic energy pulse is less than or equal to 175 mm.

In at least one embodiment, the proximal end of the cylindrically shaped space is located no more than 100 mm from a source of the acoustic energy pulse.

In at least one embodiment, the cylinder length is greater than or equal to 3 cm.

In at least one embodiment, the acoustic energy pulse comprises an acoustic shockwave pulse.

In at least one embodiment, the acoustic energy pulse is divergent or planar.

In at least one embodiment, the cylindrically shaped space is coaxial with the longitudinal axis of the acoustic energy pulse.

In another aspect of the present invention, a method of delivering an acoustic energy pulse into a body includes: providing an acoustic energy pulse generating apparatus; contacting the acoustic energy pulse generating apparatus to the body; generating the acoustic energy pulse and delivering the acoustic energy pulse into the body; wherein the acoustic energy pulse has an energy density field that can be measured at all points within a space in the shape of an imaginary cylinder having a length greater than or equal to 2 cm and a diameter; wherein the cylindrically shaped space has a proximal end, a distal end and a cylinder longitudinal axis, the cylinder longitudinal axis oriented relative to a longitudinal axis of the acoustic energy pulse at an angle in the range from zero to twenty degrees; the proximal end located at a first distance from the generating apparatus, the distal end located at a second distance from the generating apparatus, wherein the first distance is less than the second distance; and wherein a minimum energy density for the pulse at all locations within the cylindrically shaped space is at least 50% of a maximum energy density for the pulse within the space.

In at least one embodiment, the maximum energy density is in a range from 0.009 mJ/mm$^2$ to 0.044 mJ/mm$^2$, and the diameter is greater than 12 mm.

In at least one embodiment, the maximum energy density is in a range from greater than 0.044 mJ/mm$^2$ to 0.07 mJ/mm$^2$, and the diameter is greater than 13 mm.

In at least one embodiment, the maximum energy density is in a range from greater than 0.07 mJ/mm$^2$ to 0.088 mJ/mm$^2$, and the diameter is greater than 14 mm.

In at least one embodiment, the maximum energy density is in a range from greater than 0.088 mJ/mm$^2$ to 0.14 mJ/mm$^2$, and the diameter is greater than 17 mm.

In at least one embodiment, the proximal end contacts the surface of the body, and the distal end is within the body.

In at least one embodiment, the acoustic energy pulse is applied longitudinally along the length of a female urethra of the body.

In at least one embodiment, the acoustic energy pulse comprises an acoustic shockwave pulse.

In at least one embodiment, the acoustic shockwave pulse is divergent or planar.

In at least one embodiment, the contacting comprises contacting the body intra-labially and wherein the cylindrically shaped space therapeutically encompasses at least a portion of urethral sphincter muscles of an adult female human.

In at least one embodiment, the contacting comprises contacting the apparatus to the perineum of the body.

In at least one embodiment, the contacting comprises contacting the apparatus to the anus of the body.

In at least one embodiment, the method further includes mounting the apparatus to a stabilizing system.

In at least one embodiment, the stabilizing system maintains the apparatus in contact with the body with a predetermined amount of force.

In at least one embodiment, the cylindrically shaped space is coaxial with the longitudinal axis of the acoustic energy pulse.

In another aspect of the present invention, a method of treating the female urethra of a patient includes: providing an acoustic energy pulse generating apparatus; contacting the acoustic energy pulse generating apparatus to a body of the patient, in contact with or adjacent to an end of the urethra; generating an acoustic energy pulse and delivering the acoustic energy pulse into the body, in a direction along a length of the urethra.

In at least one embodiment, the urethra is treated from the end of the urethra only.

In at least one embodiment, the acoustic energy pulse has an energy density field that is dimensioned to therapeutically encompass urethral sphincter muscles of the patient; and the energy density field is configured to provide a therapeutically effective level of energy density for treatment of the urethral sphincter muscles.

In at least one embodiment, a first volume of the energy density field wherein the minimum energy density is at least 50% of the maximum energy density encompasses a second volume of at least thirty percent of the urethral sphincter muscles.

In at least one embodiment, the maximum energy density in the second volume is less than or equal to 0.11 mJ/mm$^2$.

In at least one embodiment, the maximum energy density is less than or equal to 0.09 mJ/mm$^2$.

In at least one embodiment, the maximum energy density has a value in a range from about 0.005 mJ/mm$^2$ to about 0.035 mJ/mm$^2$.

In at least one embodiment, the maximum energy density has a value in a range from about 0.035 mJ/mm$^2$ to about 0.07 mJ/mm$^2$.

In at least one embodiment, the acoustic energy pulse comprises an acoustic shockwave pulse.

In at least one embodiment, the acoustic shockwave pulse is divergent or planar.

In another aspect of the present invention, an apparatus for generating acoustic energy pulses for delivery into a living body includes: a housing comprising an opening and a longitudinal axis, wherein the longitudinal axis extends through the opening; an acoustic energy pulse generator wherein at least a portion of the acoustic energy pulse generator is contained within the housing; and a contact portion configured to be placed in contact with or adjacent to the living body, and positioned such that an acoustic energy pulse generated by the acoustic energy pulse generator passes through the contact portion; wherein the acoustic energy pulse generator is configured to generate and deliver the acoustic energy pulse along a urethra of the living body in a direction along a length of the urethra, the acoustic energy pulse being configured to produce a therapeutic result.

In at least one embodiment, the acoustic energy pulse generator comprises an acoustic shockwave generator and the acoustic energy pulse comprises an acoustic shockwave pulse.

These and other features of the invention will become apparent to those persons skilled in the art upon reading the details of the apparatus, systems and methods as more fully described below.

BRIEF DESCRIPTION OF THE DRAWINGS

In the course of the detailed description to follow, reference will be made to the attached drawings. These drawings show different aspects of the present invention and, where appropriate, reference numerals illustrating like structures, components, materials and/or elements in different figures are labeled similarly. It is understood that various combinations of the structures, components, materials and/or elements, other than those specifically shown, are contemplated and are within the scope of the present invention.

DETAILED DESCRIPTION OF THE INVENTION

Figure 1:
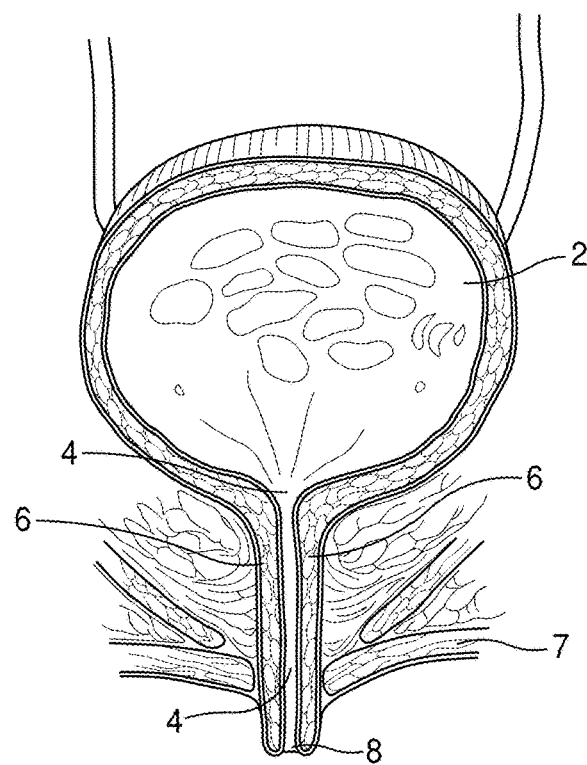
FIG. 1 illustrates the location of the urethral sphincter muscles relative to the urethra, bladder, pelvic floor muscles and urethral opening of an adult female human.

Before the present apparatus and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a pulse" includes a plurality of such pulses and reference to "the source" includes reference to one or more sources and equivalents thereof known to those skilled in the art, and so forth.

The publications discussed herein are provided solely for their disclosure prior to the filing date of the present application. The dates of publication provided may be different from the actual publication dates which may need to be independently confirmed.

Definitions

An "acoustic energy pulse" or "acoustic pulse", as used herein, refers to an acoustic compression wave that is a pulse having an initial compression phase followed immediately by an initial rarefaction phase where i) the interval between the time that the pressure in the compression phase first increases to 10% of the peak pressure in such phase until the time the negative pressure in the rarefaction phase declines to 10% of the peak negative pressure in such phase does not exceed 12 microseconds; ii) the peak pressure in the initial compression phase is at least 2.5 megapascals (MPa); and iii) the absolute value of the peak negative pressure in the rarefaction phase does not exceed 85% of the peak positive pressure in the compression phase. For example, an acoustic energy pulse may be an acoustic shockwave pulse; a pulse generated by a percussion device by accelerating a projectile into a target at high speed for the purpose of treating living tissue, wherein the projectile has a maximum width dimension (orthogonal to the direction of acceleration) that is less than or equal to 4 cm, such pulses commonly referred to as ballistic or radial shockwaves, or any other pulse having the characteristics of an acoustic energy pulse as described above.

"Acoustic shockwaves" as used herein, refer to acoustic energy pulses that move faster than the local speed of sound in the medium in which they are traveling.

"Energy flux density" or "EFD" at a point in space is defined as the amount of energy contained in a single acoustic energy pulse passing that point per unit of cross-sectional area orthogonal to the direction of pulse propagation. It is measured in $mJ/mm^2$. All EFD measurements referred to herein are calculated from pressure measurements of acoustic pulses as they pass through water. The pressure of the pulse at a point in space and time in a water tank is measured with a hydrophone located at that point in space. The hydrophone emits a voltage which varies with water pressure over time. The voltage signal is digitized and converted into a pressure curve by applying the voltage/pressure relationship of the hydrophone. The EFD of the pulse is computed by integrating the square of the pressure curve over time according to formula 7.2.3 of International Electrotechnical Commission (IEC) Standard 61846:1998, as follows:

At a spatial point (x,y,z), wherein z, y and z are the three dimensional coordinates of the spatial point:

$$EFD(x,y,z)=1/Z\int_T \rho^2(x,y,z,t)dt \quad (1)$$

where EFD is energy flux density, in $J/m^2$. Conversion of the EFD values obtained in formula one to values having units of $mJ/mm^2$ can be performed by dividing by 1000;

Z is a factor characterizing the acoustic impedance of the medium (e.g. water, for the instant application), in PA-sec/m where Z is equal to the density of the medium times the speed of sound in the medium;

The temporal limits over which integration is performed, T, should be stated and can be either $T_P$ or $T_T$ where:
$T_P$=times between which the positive acoustic pressure first exceeds 10% of its maximum value and the first time it reduces below 10% of its maximum value; and
$T_T$=times between which the absolute value (modulus) of pressure pulse waveform first exceeds 10% of its maximum value and the last time it reduces below 10% of its maximum value;
$\rho$=the instantaneous acoustic pressure in Pa; and
t=time in seconds.

All EFD values for apparatus disclosed in regard to the present invention herein are based on measurements from three hydrophones. An initial pressure curve was derived using a Mueller-Platte 100-100-1 PVDF Needle Probe (Mueller Instruments, Oberursel, Germany) with the manufacturer's specified sensitivity. Formula 7.2.3 of IEC 61846:1998 was applied with $T=T_T$ to calculate EI-D. No frequency response adjustment was made in converting probe voltage to pressure. Additional pressure curves were derived at selected reference points using the ONDA HFO fiber optic hydrophone and the ONDA HNR ceramic hydrophone (both from Onda Corporation, Sunnyvale, California, USA) using frequency domain adjustments specified by the manufacturer. These pressure curves were converted to EFD by applying formula 7.2.3 of IEC 61846:1998 with $T=T_P$ which is common industry practice. The reference EFD values of the two ONDA hydrophones were in substantial agreement, but were 175% higher than the Mueller-Platte hydrophone values. This is ascribed to low sensitivity of the Mueller-Platte hydrophone at lower frequencies which causes understatement of pressure for the type of pulses generated by the apparatus disclosed herein. All EFD values derived from the Mueller-Platte hydrophone were increased by 175% to correct for the pressure understatement.

"Low energy acoustic pulse" ("LEAP") therapy, as used herein, refers to treatment comprising application of one or more acoustic energy pulses having a relatively low energy for the treatment of tissue. "Relatively low energy" is defined here as being in an EFD range from $0.008/mm^2$ to $0.4 \ mJ/mm^2$.

An "energy density field" refers to a space through which an acoustic energy pulse travels together with the EFD values at all points within the space.

A "cylinder", as used herein, refers to an imaginary cylinder used for purposes of calculating or defining a portion of an energy field produced by an acoustic energy pulse generator. Thus an imaginary cylinder is described as filling a specific volume portion of the energy field. Preferably the central longitudinal axis of the cylinder is coaxial with, or as near as coaxial with as possible, the longitudinal axis of the acoustic energy pulse, but may be oriented such that the cylinder longitudinal axis is within a range of zero to twenty degrees relative to the longitudinal axis of the acoustic energy pulse.

"Treatment" or "treat" as used herein, refers to application of one or more pulses of low energy acoustic energy to facilitating rebuilding, regenerating, strengthening and/or returning target tissue being treated to a normal functioning condition or to a condition closer to normal functioning than its condition prior to treatment.

A "therapeutic result" or "successful therapeutic result" as used herein, refers to an improvement in the rebuilding, regenerating, strengthening and/or returning target tissue being treated, by an improvement of at least 30% of a value associated with any of the aforementioned characteristics prior to treatment. For treatment of UI, one non-limiting method of measuring a therapeutic result is the twenty-four hour pad test, where a patient is instructed to wear a pad for twenty-four hours prior to treatment and the pad is weighed after the twenty-four hours and compared to the weight of a dry pad to determine the weight of the urine that has been leaked. After treatment, the same procedure is carried out and the weight of the urine in the pad after treatment is compared to the weight of the urine in the pre-treatment pad to determine the difference. A percentage of improvement can then be calculated by dividing the urine weight difference by the pre-treatment urine weight and multiplying by 100. Alternatively, a one hour pad test involves having the patient drink a predetermined volume of water and then move vigorously over a predetermined time period, typically about an hour. This procedure can be followed both pre- and post-treatment, with urine weights determined from the pre- and post-treatment pads to calculate a percentage improvement in the same way as calculated in the twenty-four hour test. It is noted that measures of determining therapeutic effectiveness are in no way limited to these two techniques, as they are only provided as examples. Of course, these tests would not even be applicable for treatment of tissues or organs other than the urethra. A reduction in urine weight by at least 30% between the pre- and post-treatment pads for either the twenty-four hour or one-hour test would be a "therapeutic result" or "successful therapeutic result" as used herein.

"Therapeutically effective" refers to a treatment having characteristics that are sufficient to provide a successful therapeutic result when treating a patient.

"Therapeutically encompass" refers to encompassing a target tissue or organ in full or encompassing at least a portion of such with an energy field that is sufficient to result in a therapeutically effective treatment of the target tissue organ.

"Urinary incontinence" ("UI") is defined as the involuntary leakage of urine. There are two basic types of UI: stress incontinence and urge incontinence. Stress incontinence ("SUI") is caused by the inability of the urethral sphincter muscles to keep the urethra closed when pressure is applied to the bladder such as during exercise, sex, coughing or through sagging of the pelvic organs. Urge incontinence ("UUI") is caused by involuntary contraction of the urinary bladder muscles.

"Unfocused" as applied to energy fields produced by acoustic energy devices, as used herein, refers to an energy field in which the EFD decreases or is constant in every direction away from the source of the acoustic energy generation.

DETAILED DESCRIPTION

When LEAPs are applied at appropriate energy level, frequency and duration, they can stimulate the growth of new tissue and thereby repair and regenerate damaged and diseased tissues/organs. The present invention is directed toward specialized apparatus and methods for generating the appropriate energy levels, frequencies and durations of LEAPs and to deliver them to target tissue to effect repair and/or regeneration of the target tissue.

The present methods and apparatus, when used according to the details provided herein, activate naturally occurring stem cells and progenitor cells which reside in nearly every soft tissue in the body. Once activated, the stem cells and progenitor cells begin to divide and differentiate into new adult cells, just as they do during normal growth and healing processes. Stem cell therapy is considered to be one of the most promising areas in medicine. However, conventional approaches require tissue removal, enzyme digestion, isolation and re-implantation of stem cells into the body. These procedures are fraught with difficulty and have had limited clinical success. The present apparatus and methods can be effective to realize the potential of stem cell therapy non-invasively, safely, relatively painlessly and at a small fraction of the cost of conventional stem cell therapy.

Therapeutic ranges of combinations of energy level, frequency and duration are specific to various types of tissues. Combinational values which are too low (and thus below the therapeutic range) for a particular type of tissue do not result in the desired activation of stem and progenitor cells when applied to the tissue, while combinational values which are too high (and thus above the therapeutic range) can cause tissue damage.

LEAP therapy represents a new approach to treating injury and degenerative diseases as it harnesses the body's innate repair mechanisms non-invasively, safely and with no pain. No drugs, needles, implants or invasive surgery are required. Apparatus according to the present invention, used to apply LEAP therapy in the therapeutic range to a target tissue as described according to the present methods can effectively, safely and less expensively treat injury and degenerative diseases of the body.

The present invention can be applied to treat urinary incontinence (UI), for example, SUI and/or UUI.

Regarding female UI, epidemiological studies have indicated that approximately ⅓ of all adult women (which is about 39 million U.S. women) experience some form of UI. The incidence rate increases with age although younger women often experience UI after childbirth. UI affects women's lives to varying degrees, depending upon the severity of the condition. At a minimum it is a nuisance and inconvenience. At worst it is a cause of embarrassment, discomfort and inability to function professionally and socially. One indicator of the extent of the problem is that approximately fifteen billion adult diapers are sold in the U.S. each year, the majority of which are used for female urinary incontinence.

Stress incontinence represents approximately half of all cases of female UI. Mixed incontinence, a combination of stress incontinence and urge incontinence, represents another 30% of all cases of female UI. Altogether roughly 80% of female urinary incontinence cases involve weak urethral sphincter muscles. FIG. 1 illustrates the location of the urethral sphincter muscles 6 relative to the urethra 4, bladder 2, pelvic floor muscles 7 and urethral opening 8 of an adult female human.

Urge incontinence can be treated with drugs and neurostimulation devices, both of which modulate the nerve impulses that cause involuntary bladder contraction. Success rates range from 50% to 80%, although 30% of patients stop taking the drugs due to side effects. There are currently no effective treatments for stress incontinence other than surgery. Surgery compensates for weak urethral sphincter muscles by supporting the urethra with an implanted strip of material. Success rates average 80% when the procedure is performed by a skilled urological surgeon. However, manufacturers of the surgical material have promoted the procedure aggressively to doctors without the requisite skill and training. Failures are common and manufacturers are facing 1.5 billion in lawsuits over their surgical mesh products, albeit primarily for their use in earlier UI procedures. Surgery for stress incontinence is also expensive, averaging $35,000 per outpatient procedure and $49,000 per inpatient procedure.

The present invention provides an alternative to the above described disadvantages of treatment of female UI, and especially female SUI with surgery. The present apparatus and methods may be used to rebuild and strengthen the urethra sphincter muscles sufficiently to enable them to keep the urethra closed under typical stress conditions. Although treatment of the female urethral sphincter muscles is the primary focus of the present invention, the present invention is not limited to this application, as the male urethral sphincter muscles may be treated, and or other sphincters or soft tissues in the urinary system and/or anal region, or any tissue located at or near the surface of the body which extends into the body, including but not limited to the penis.

Although apparatus for generating acoustic pulses such as shockwaves are known, there are no existing apparatus known to the present inventors that can deliver the desired level of energy (in the therapeutic range) along the length and width (in all directions encompassing the diameter) of the urethra and therapeutically encompassing the urethral sphincter muscles so that the urethral sphincter muscles are effectively treated over the extent thereof from a stationary apparatus. It is believed that a predetermined level of energy needs to be delivered all along the urethra/urethral sphincter muscles (or a portion thereof sufficient to effect a therapeutic treatment), in order to effect repair and regeneration in the manner described above. The original lithotripters focus high energy shockwaves on kidney stones to overcome the tensile forces holding the stones together and thereby shatter them. This focused energy is strong enough to damage most tissue. Low energy shockwaves were experimented with for at least fifteen years to determine whether they could be used therapeutically. Only four low energy shockwave devices have been approved for sale in the U.S.—three for treatment of orthopedic conditions such as tennis elbow and plantar fasciitis and one for treatment of diabetic foot ulcers. In all devices currently known to the inventors, even including those that may be referred to as "unfocused", there is actually a focal point away from the probe/source of the shockwave. To applicant's knowledge nowhere in the world have any devices been approved for sale for treatment of female urinary incontinence. Nor have any devices been proposed which have been optimized for treatment of the female urethra for urinary incontinence. No known devices are capable of therapeutically encompassing the female urethra in an energy field, simultaneously with effective and appropriate amounts of energy applied at all locations of the urethra and urethral sphincter muscles within the field, so as to effect a therapeutic result from the application of such energy. To applicant's knowledge, prior to the present invention there were no truly unfocused shockwave devices available in the market. The present invention provides an unfocused LEAP device.

For longitudinal application of LEAPs along the female urethra, the probe that delivers the LEAPs must be relatively small to fit comfortably between the legs of the patient to which the LEAPs are to be delivered. Because of this constraint currently known shockwave applicators are either too large, or, if not too large, cannot deliver an energy field having sufficient EFD and EFD consistency to effectively deliver a therapeutic treatment longitudinally along the female urethra.

All shockwave generators employ the principle of converting a high voltage pulse of electricity into a mechanical pressure wave inside a water filled cavity, typically defined in a probe of a treatment apparatus. The pressure wave is shaped and directed through a plastic membrane on one side of the cavity. The membrane is placed against the skin of the patient being treated with a layer of hydrogel typically interspersed between the membrane and the skin to facilitate transmission of the acoustic pulses (e.g., shockwaves). Most known apparatus can generate one, three, five or more pulses per second. The pressure waves (e.g., shockwaves) propagate through soft tissue due to the water content of the soft tissue.

The energy density of the shockwaves or other low energy acoustic pulses depends on the amount of energy discharged in each electrical pulse and the cross-sectional area of the pressure wave. Currently available shockwave generators typically boost the energy density by focusing the waveform into a narrower cross-sectional area. The focus is also longitudinal. All shockwave generators currently known to the inventors, prior to the present invention, focus the waveform into a narrower cross-sectional area. Some of these prior art devices have been characterized by their manufacturers as "unfocused" of as capable of delivering a "planar or divergent" wave, but in fact, even these devices focus the waveform to some degree. In contrast, the present invention generates waveforms that are completely unfocused.

Figure 2A:
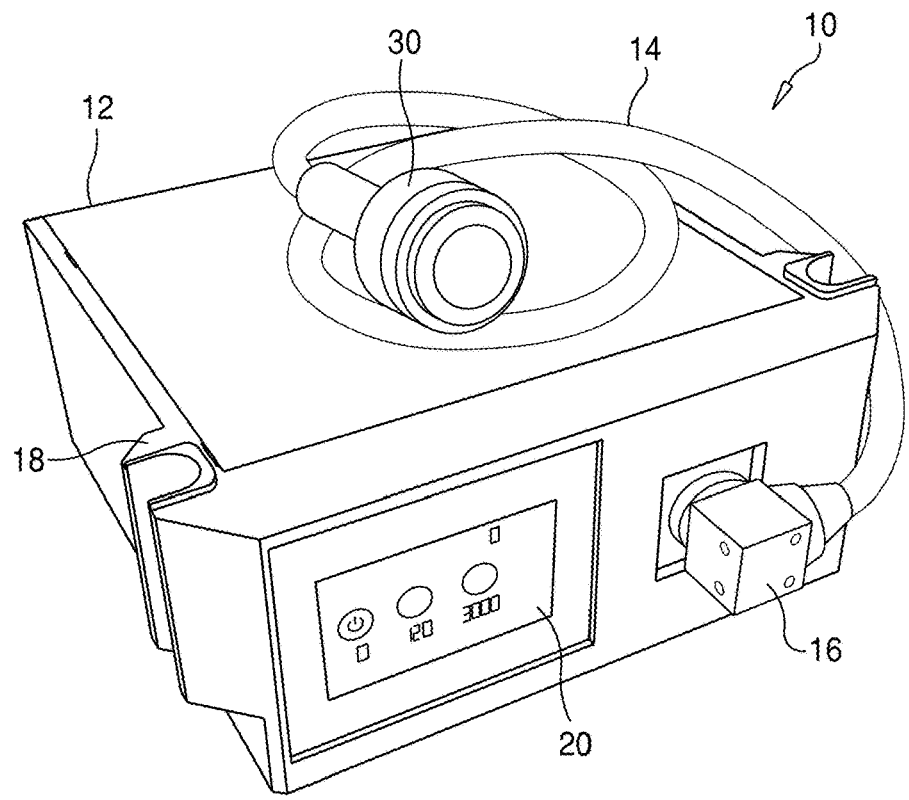
FIG. 2A is a perspective view of a low energy acoustic pulse (shockwave) LEAP apparatus according to an embodiment of the present invention.
Figure 2B:
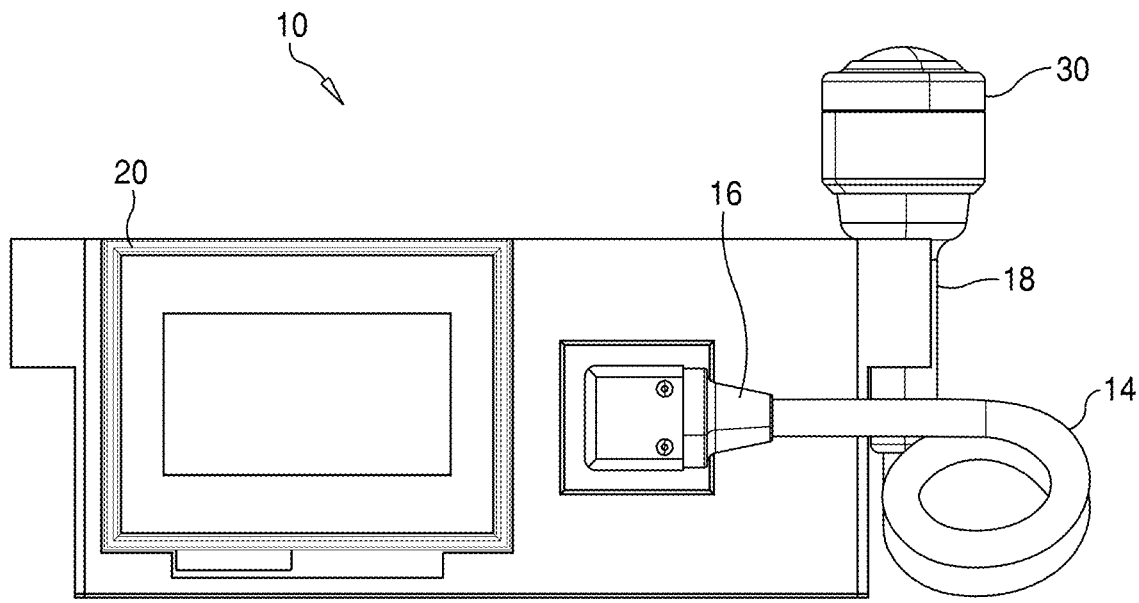
FIGS. 2B and 2C are front and rear views of the apparatus of FIG. 2A.
Figure 2C:
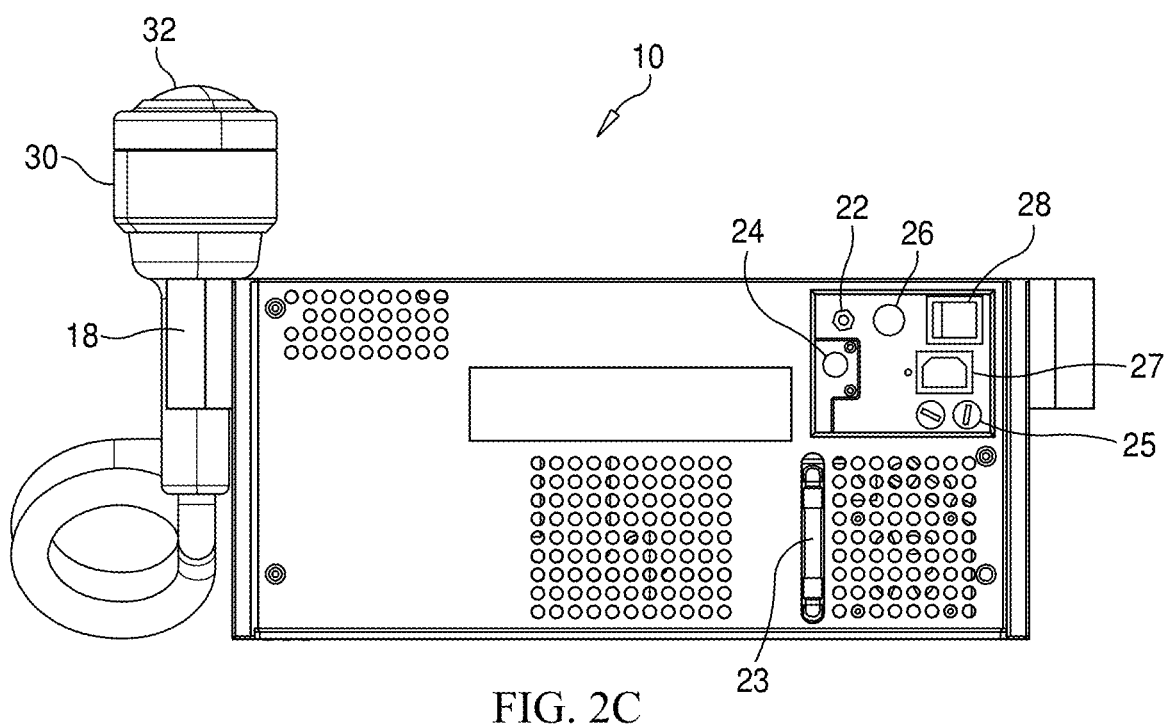

FIG. 2A is a perspective view of a low energy acoustic pulse (shockwave) LEAP apparatus 10 according to an embodiment of the present invention. FIGS. 2B and 2C are front and rear views of the apparatus of FIG. 2A. Apparatus 10 includes a control unit 12 that contains the electronics required to control the probe 30. The probe 30 is electrically connected to the control unit by cable 14 and electrical connector 16. A probe holder or place rack 18 may be provided on the control unit 12 to hold the probe 30 when not in use, as illustrated in FIG. 2C. A display (preferably, but not necessarily a touch panel) 20 can be used to interactively control the apparatus, as well as display operating conditions of the apparatus and other data. A ground outlet 22 is provided on the back of the control unit case to be connected to ground for grounding the apparatus to avoid electric shock. A fluid tank filling pipe terminal 24 is provided for filling the tank of the apparatus with water. A foot switch terminal 26 can optionally be provided to allow an optional foot switch to be connected to the apparatus for allowing the operator to fire the apparatus with a foot operated command. However, these optional features are not necessary to making and using of the present invention, and are presently not preferred. Power switch 28 allows the operator to turn the power to the apparatus on and off. A power supply jack 27 receives the power cord that is also connectable to a source of electric power. Fuse block 25 is provided to protect the circuitry of the apparatus. Indicator 23 indicates the level of fill of the water tank. A water cushion 32 may be provided at the distal end portion of the probe 30 as described in more detail below.

There are at least three different techniques for generating shockwaves. The three techniques are electrohydraulic, electromagnetic and piezoelectric and all of these techniques are effective to convert electrical energy to mechanical energy. A further description of the physics and principles by which these three techniques operate can be found in Ogden et al., "Principles of Shock Wave Therapy", Clinical Orthopedics and Related Research, Number 387, pp. 8-17, 2001, which is hereby incorporated herein, in its entirety, by reference thereto. Another type of therapeutic low energy acoustic pulse, commonly referred to as a ballistic shockwave or radial shockwave, is produced by accelerating a metal projectile along a barrel with compressed air. The projectile strikes a metal target at the end of the barrel and creates a compression wave that is conducted to tissue contacting the opposite side of the target.

Figure 3A:
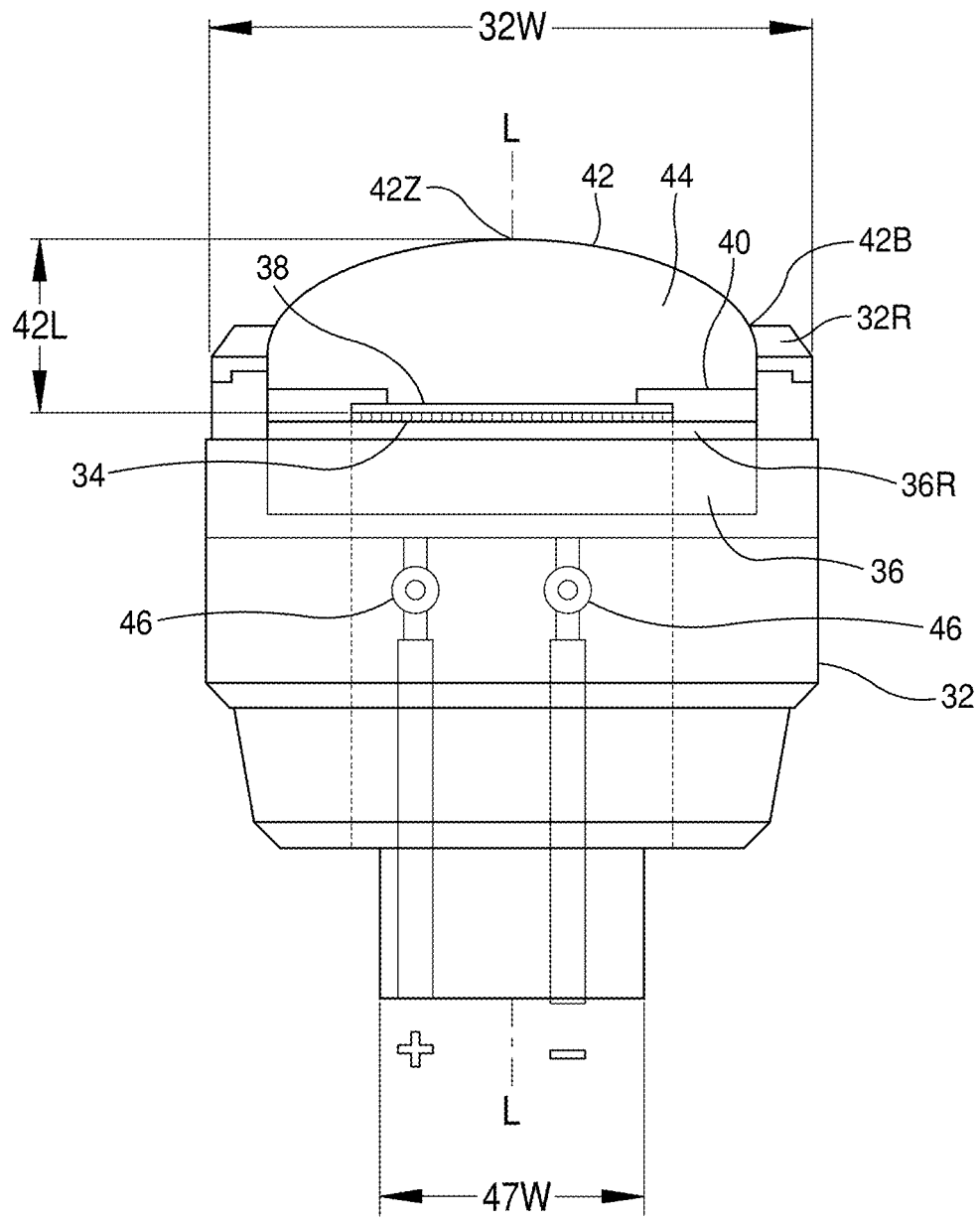
FIG. 3A is a schematic representation of a cutaway view of a portion of a probe according to an embodiment of the present invention.

FIG. 3A is a schematic representation of a cutaway view of a portion of probe 30 according to an embodiment of the present invention. The present invention preferably employs the electromagnetic generation principle to generate LEAPs, as exemplified by the embodiment of FIG. 3A, but is not limited to this technique, as others described herein and equivalents thereof could be used if capable of performing to the specifications described herein. Housing 32 contains components of the probe and is configured to be grasped by the hand of an operator. The width 32W of the housing 32 should be kept to a minimum while still being capable of containing components capable of generating and delivering LEAPs having the specifications described herein, so as to adequately treat the target tissue that the present apparatus is designed to treat. In this embodiment, the apparatus is designed for treatment of the female urethra and width 32W is less than or equal to about 140 mm, preferably less than or equal to about 125 mm, even more preferably, less than about 100 mm. In some embodiments, the width 32W is less than or equal to 90 mm, and in some embodiments, width 32W is in the range from about 70 mm to about 90 mm.

Figure 3B:
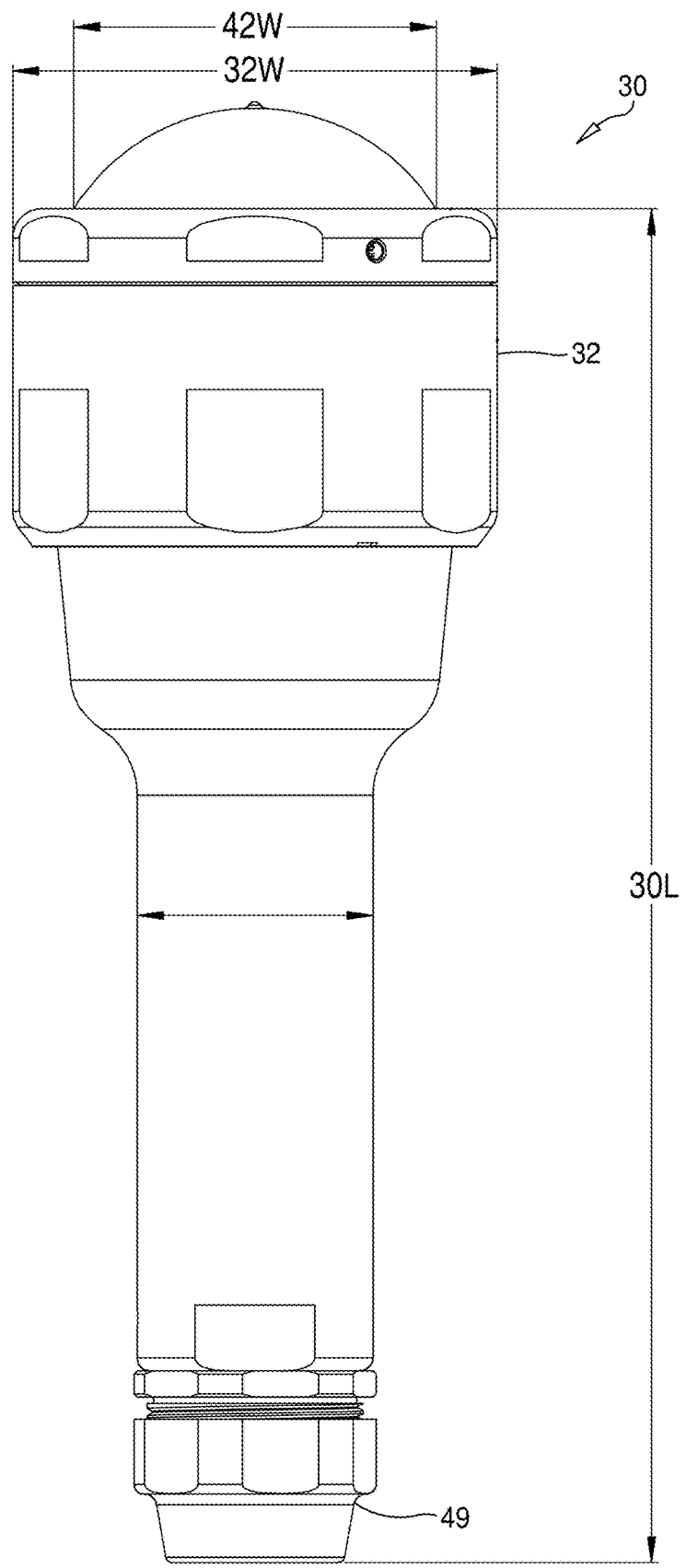
FIG. 3B is a side view of a probe according to an embodiment of the present invention.
Figure 3C:
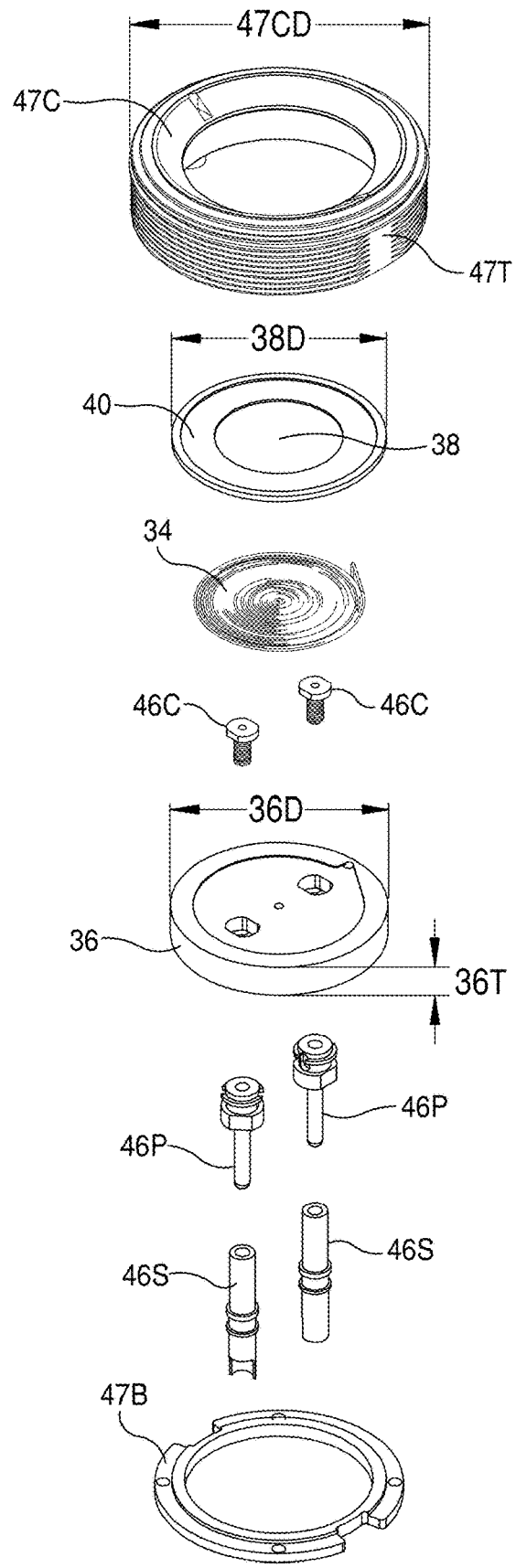
FIG. 3C is an exploded view of components of the probe of FIG. 3B, according to an embodiment of the present invention.
Figure 3D:
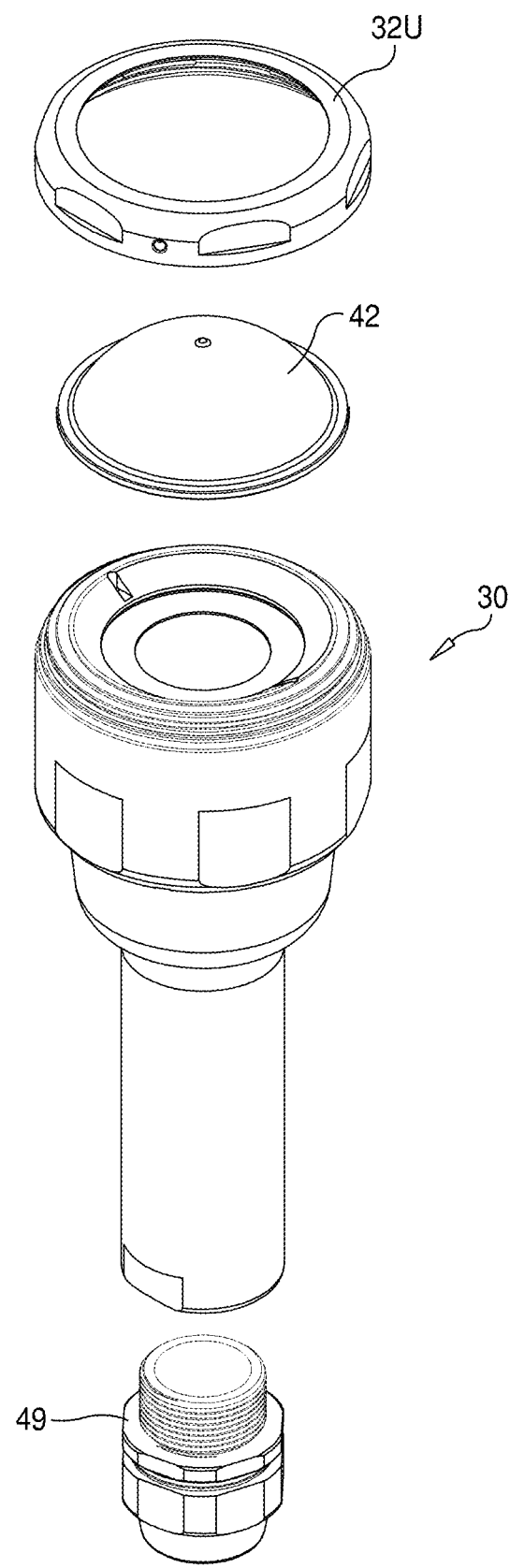
FIG. 3D is a partially exploded view of the probe of FIG. 3B.

In one particular example of an embodiment acceptable for treatment of the female urethra as shown in FIGS. 3B-3D, the width 32W was about 74 mm. The exposed width 42W of the flexible diaphragm was about 54 mm, but this width can also vary in proportion to variation in the width 32W. In another particular example also acceptable for treatment of the female urethra as described herein and shown in FIGS. 3F-3H, the width 32W was about 88 mm Preferably, in all embodiments, the housing 32 is substantially cylindrical, with a longitudinal axis aligned with the longitudinal axis L-L of probe 30, but alternatively the housing could be oval, elliptical, polygonal or some other shape, as long as it can be fit comfortably between the legs of the patient and applied as described. Accordingly, smaller widths of the device housing are preferred. Unlike electromagnetic shockwave devices currently available in the market, probe 30 emits unfocused LEAPs and does not employ a lens.

Figure 3E:
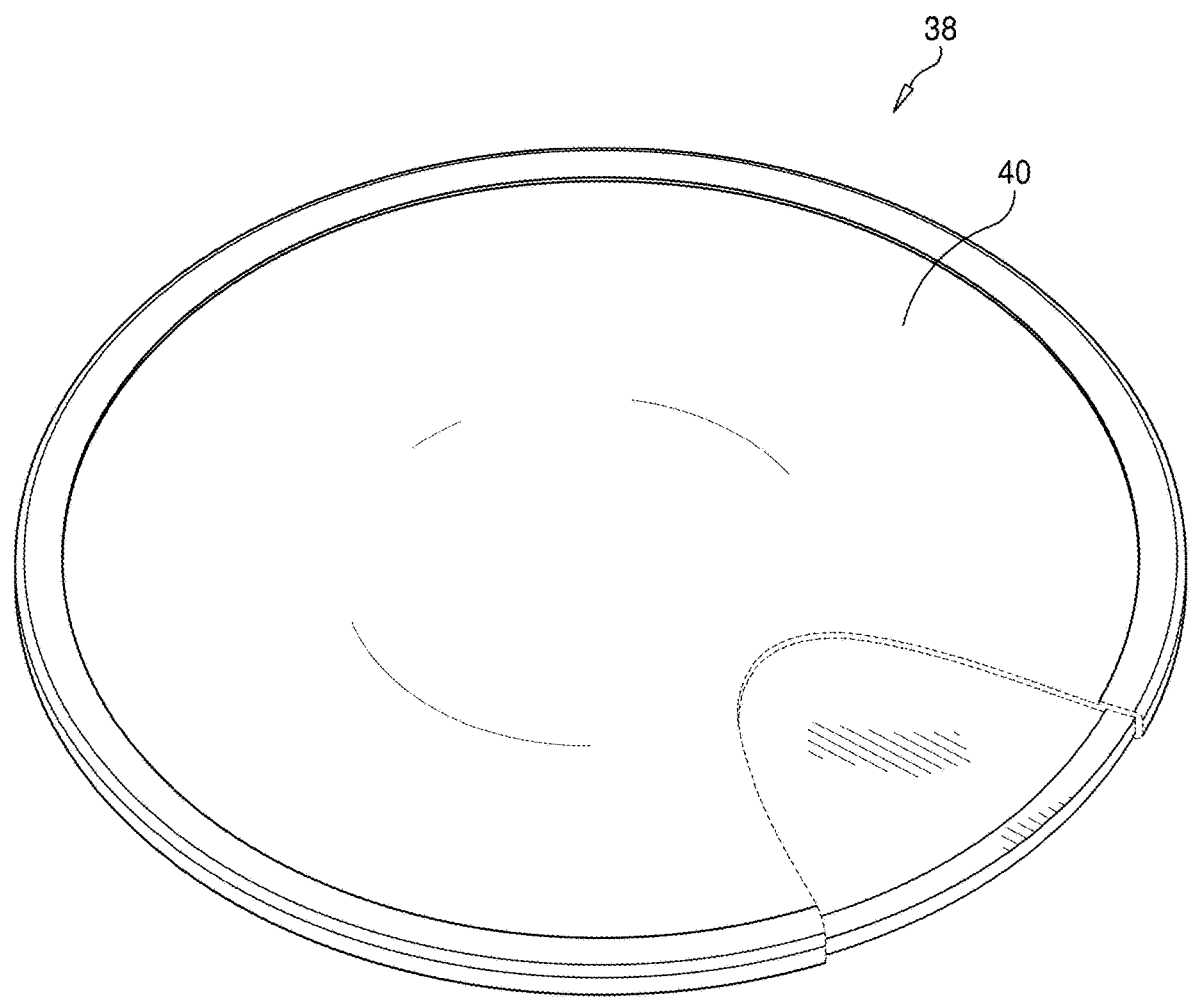
FIG. 3E shows a top view of a driver completely coated on its top side with a coating according to an embodiment of the present invention.
Figure 3F:
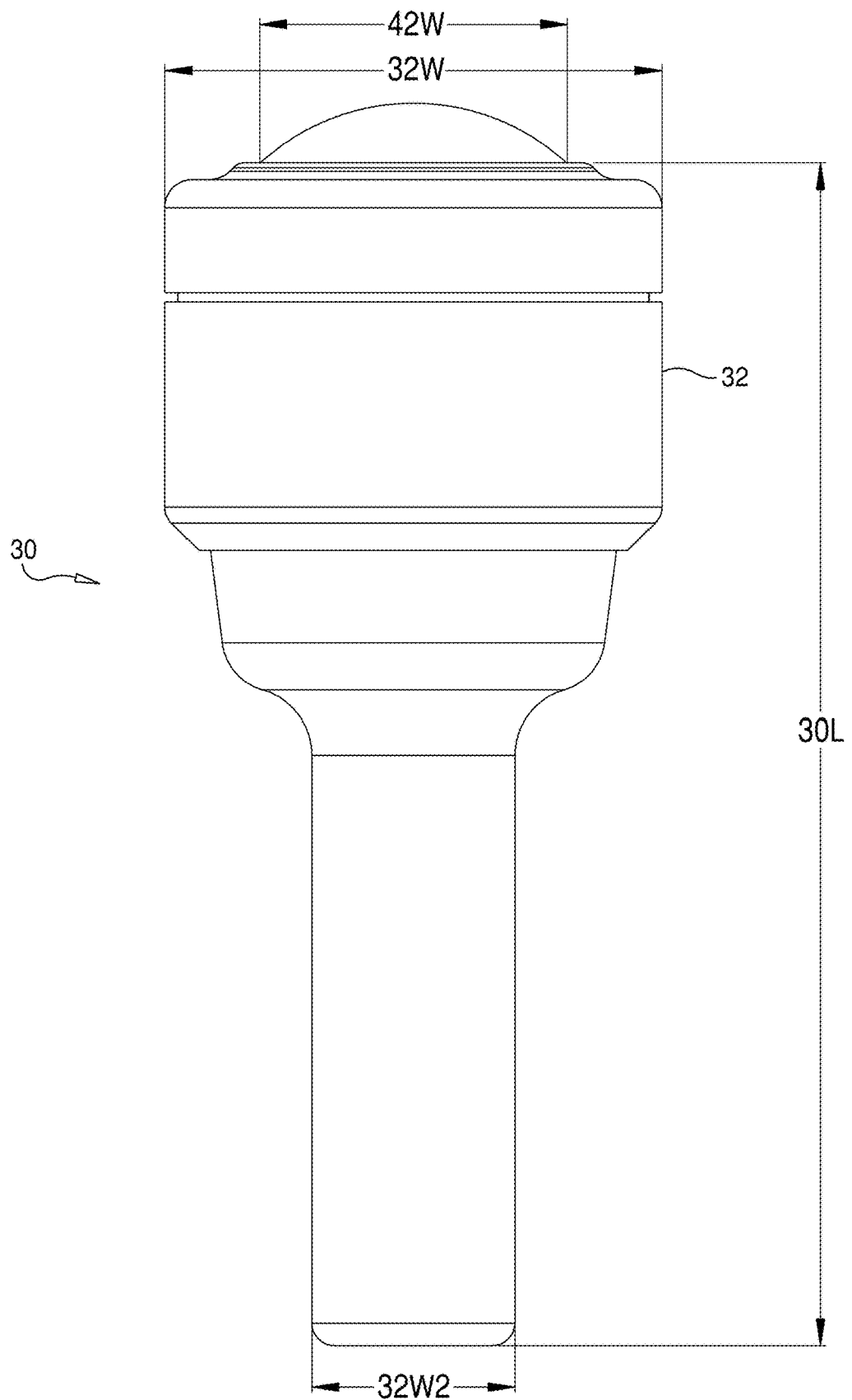
FIG. 3F is side view of a probe according to another embodiment of the present invention.

As noted, the LEAP generators of the probes 30 according to the embodiments of FIGS. 3A-3H are configured to generate LEAPs by the electromagnetic principle. A coil 34 (FIGS. 3C and 3G) is mounted to a substrate 36 held by housing 32 (FIGS. 3B and 3F). The substrate 36 may be a glass reinforced epoxy laminate such as FR4 (glass-reinforced epoxy laminate; composite material composed of woven fiberglass cloth with an epoxy resin binder that is flame resistant/self-extinguishing) or other material that can perform in a similar manner as an insulator. The coil 34 in at least one embodiment is mounted to the substrate 36 by an adhesive. Additionally, or alternatively, coil 34 may be adhered to substrate 36 with a resin layer 36R that can any of the same materials described below for use in coating the coil 34. The substrate 36 is typically in the shape of a circular disk, but is not limited thereto and could have other shapes, such as oval, ellipsoid, rectangular or other polygonal, or other shape. The substrate 36 has an outer dimension (outside diameter, when circular disk-shaped) that is only slightly greater than that of the driver 38. The outer dimension/outside diameter 36D of substrate 36 can be in a range from about 4.0 cm to about 8.5 cm, preferably from about 4.5 cm to about 7.5 cm. In the example shown in FIG. 3C, outside diameter 36D was about 5.6 cm and had a thickness 36T of about 8 mm Thickness 36T may be in a range from about 3 mm to about 16 mm. In the example shown in FIG. 3G, outside diameter 36D was about 6.3 cm and had a thickness 36T of about 14 mm.

Coil 34 can be coated with a resin 36R that provides additional electrical insulation between the windings of the coil and helps hold the coil in place. Resins with high dielectric strength such as resins 74050T or 724F2 from Von Roll USA, Inc. are preferred. In at least one embodiment, coil 34 comprises enameled copper wire having a diameter in the range from about 0.25 mm to about 1.0 mm, preferably in a range from about 0.4 mm to about 0.7 mm. In the examples shown in FIGS. 3C and 3G, coil 34 comprised copper wire having a diameter of 0.55 mm.

Figure 3G:
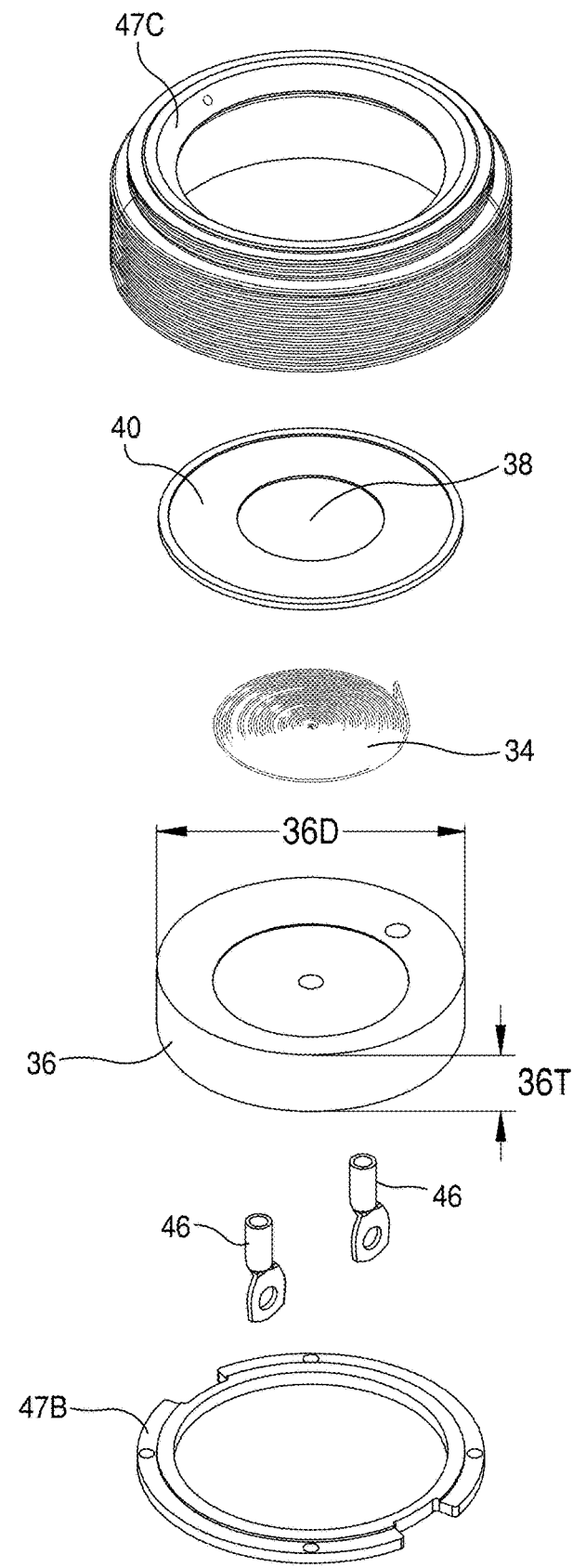
FIG. 3G is an exploded view of components of the probe of FIG. 3F.

A driver 38 preferably in the form of a metallic disk is mounted on coil 34 as shown in FIG. 3A. In at least one embodiment, driver 38 is a circular disk made of high performance aircraft grade aluminum. One such embodiment is 7075 T6 aluminum. Of course the present invention is not limited to this specific material, as substitutes could be used. The diameter of the driver 38 typically is less than or equal to the width of the coil 34 and of course, less than the width 32W of the housing 32. In at least one embodiment, the diameter is about 5 cm. In at least another embodiment, the diameter of the driver is about 6 cm. Alternatively, the diameter could be in the range of from about 3.5 cm to about 8.0 cm, preferably from about 4.0 cm to about 7.0 cm, or 3.5 cm to 6.5 cm, or 4.0 cm to 6.0 cm or 4.5 cm to 5.5 cm, or any other range within the range of 4.0 cm to 7.0 cm. In the example shown in FIG. 3C, driver 38 diameter 38D was about 5 cm (i.e., 4.99 cm) and the thickness of 40 and 38 together was about 1.5 mm, with the driver 38 having a thickness of about 0.6 mm. In the embodiment of FIG. 3G, driver 38 diameter 38D was 6.22 mm and had a thickness about the same as that of the embodiment of FIG. 3C. The combined thickness of 38 and 40 was about 1.5 mm. The thickness of the driver 38 may be in a range from about 0.4 mm to about 1.0 mm. Further alternatively, other metals able to produce pulses of sufficient strength could be used to make the driver, although they would likely result in a shorter life cycle prior to failure of the driver 38. In a preferred embodiment, driver 38 is configured to fire at least 100,000 pulses, more preferably 400,000 to 1.5 million pulses prior to failure, more preferably 500,000 to 1.25 million, even more preferably 750,000 to 1.1 million, and, in some embodiments, 1 million or more. The lifetime of the driver 38 will vary depending upon the energy levels that are produced by the LEAPs. In at least one embodiment the lifetime of the driver 38 can exceed 1.2 million pulses when producing an EFD of 0.035 mJ/mm$^2$. In at least one embodiment the lifetime of the driver 38 can be in the range from about 700,000 to about 1 million pulses when producing an EFD of 0.088 mJ/mm$^2$.

A resilient gasket 40 (e.g., see FIGS. 3C and 3G), for example, typically rubber, forms a ring-like structure that retains the driver 38 around its perimeter such that driver 38 is retained in position adjacent to the coil 34, while at the same time allowing the driver 38 to move (as well as deform) when the coil 34 fires to generate a LEAP. Gasket 40 may be injection molded around the driver 38 during manufacture, or alternative methods of joining may be used, including, but not limited to adhesives, soldering, welding, mechanical fixation, or the like. Alternatively, resilient gasket 40 may completely cover at least the top side of the driver 38, as illustrated in FIG. 3E. In this variant, the resilient gasket 40 acts as a top coating that seals the top of the driver. Further alternatively, the driver may be completely encased in the resilient gasket 40 material, such that the material 40 coats all of the driver 38. Further alternatively, at least both top and bottom surfaces of the driver 38 may be completely coated with the resilient gasket 40 material. The coating prevents or lessens cavitation erosion of the metallic disk material of the driver 38 that can occur with repeated generations of LEAPs, thereby extending the useable lifetime of the driver 38.

A flexible diaphragm or membrane 42 encloses the otherwise open distal end of the housing 32. Flexible diaphragm 42 is configured to contact the body during use to provide an atraumatic interface with the body while allowing a LEAP to pass therethrough. The length or height 42L of the distal surface of the flexible diaphragm 42 from the driver 38 is adjustable by adding or removing fluid (water or saline or other liquid that facilitates transmission of LEAPs and is preferably biocompatible) from the chamber 44 that forms a cushion as enclosed by the flexible diaphragm. A fluid reservoir (not shown) is provided in apparatus 10 and can be filled via fluid tank filling pipe terminal 24 (see FIG. 2C). Fluid can be removed from or added to the fluid cushion 44 to decrease or increase the length/height 42L by operation of the touch screen 20 to control operation of a fluid pump (not shown) within the apparatus 10, so that fluid is delivered through or withdrawn from the chamber 44 via cable 14, which includes a lumen that connects the fluid reservoir in fluid communication with the chamber 44. Thus the length/height can be set to the desired parameter.

The range of heights/lengths (measured from the base 42B of the fluid cushion 42 at the top of the device rim 32R to the zenith 42Z of the fluid cushion 42 as illustrated in FIG. 3A) can be adjusted to is generally from about 0 cm to about 10 cm, in some embodiments from about 1 cm to 8 cm, in some embodiments from about 3 cm to 5 cm, in other embodiments from about 0 cm to 5 cm, although other ranges could also be employed. Typically, the length/height 42L is adjusted for good contact and a comfortable fit against the tissue where treatment is being performed, and is preferably in a range of from about 3 cm to about 6 cm, typically about 4 cm. In at least one preferred embodiment 42L is 4.6 cm. Variation in the length/height 42L directly affects the placement of the treatment zone of the energy density field, as described in more detail below.

A pair of terminals 46 is connected to power supply lines to provide electrical power to the coil 34. FIG. 3C shows a partial, exploded view of the probe 30 embodiment shown in FIG. 3B. As shown in FIG. 3C, the terminals 46 may include a pair of pins 46P that are received in sockets 46S that are connected to power supply lines. The pins 46P are connected to the substrate 36 via connector 46C such as screws or the like, which connect electrically with coil 34. In the example of FIGS. 3B-3D, connectors 46C are screws, although other types of connectors, including, but not limited to bolts, rivets, nails or the like could be used. The coil 34 is electrically connected to the terminals 46P, typically by soldering.

Control of the electrical power is provided by programming contained within the apparatus, with parameters such as energy level and frequency being selectable by the operator via touch panel 20. Additionally, or alternatively, mechanical means, such as control knobs or the like, can be provided for selecting EFD settings and frequency. In at least one embodiment, a plurality of EFD settings are provided for selection by the operator. EFD output is determined by the voltage applied to the coil. In one embodiment a technician can assign voltage levels to establish the EFD settings by selecting a single voltage setting (typically the setting for level 1, the lowest level, but could alternatively be the setting for the highest level or for some predetermined intermediate level) and also specify a voltage delta for the difference in voltage between adjacent settings. For example, in one particular embodiment, ten energy level settings are provided. By selecting setting 1 at 5,500 V and selecting a voltage delta of 500 V, this results in setting 1 providing 5,500 V, setting 2 providing 6,000 V, setting 3 providing 6,500 V, setting 4 providing 7,000 V, setting 5 providing 7,500 V, setting 6 providing 8,000 V, setting 7 providing 8,500 V, setting 8 providing 9,000 V, setting 9 providing 9,500 V and setting 10 providing 10,500 V. The resulting EFD levels from the voltage assignments are identified to the user in connection with the setting levels. It is noted that this is just one specific embodiment and that the present invention is not limited to this particular number or settings, or to the voltage levels assigned to any one or all of the settings. Additionally, the apparatus 10 can be reprogrammed to assign higher or lower voltages settings to one or more setting levels. For example, setting 1 can be reprogrammed as low as 4,500 V.

Figure 2D:
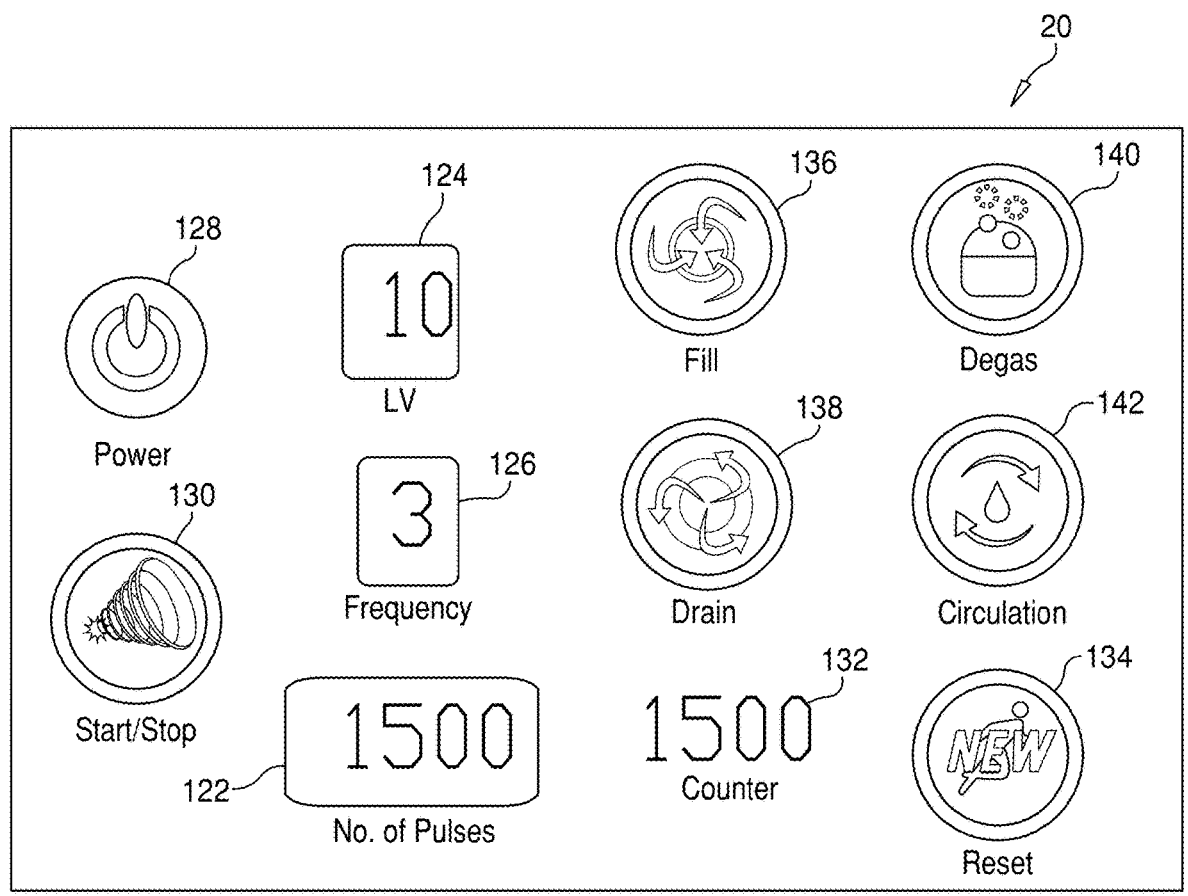
FIG. 2D is a more detailed view of the display of the apparatus of FIGS. 2A-2C.

The actual emission or "firing" of a LEAP can be actuated through the display (e.g., touch panel) 20. The display 20 is powered on by turning on the main power switch 28. The power button icon 128 (FIG. 2D) on the touch panel 20 is actuated to turn on the high voltage circuit that powers the LEAP generation. The number of pulses to be fired in a session is selected at 122. The energy level is selected at 124 and the frequency (pulses per second) is set at 126. The LEAP firing session begins upon actuating the start icon 130. A counter 132 keeps track of the actual number of pulses that have been fired during the session. LEAP firing automatically stops after the total number of LEAPs selected have been fired. The reset button icon 132 resets the counter to zero. The fill icon 136 is selected to add fluid to extend 42, while actuation of drain 138 retracts 42. The degas 140 is used for removing air bubbles from the fluid and the circulation icon is used for circulating the fluid in connection with cooling functions beyond the scope of the present invention. Frequency of firing can be set to a value within a range from 1 Hz to 10 Hz, preferably from 1 Hz to 8 Hz, more typically from 1 Hz to 6 Hz, with current preferences for 3 Hz and 5 Hz selections. The number of pulses can be selected in the range of 1 to 1500, but this could vary. The power source that the apparatus is powered by can be a 110V power source, such as an outlet. Alternatively, other power sources, including, but not limited to 220V, could be used.

Figure 3H:
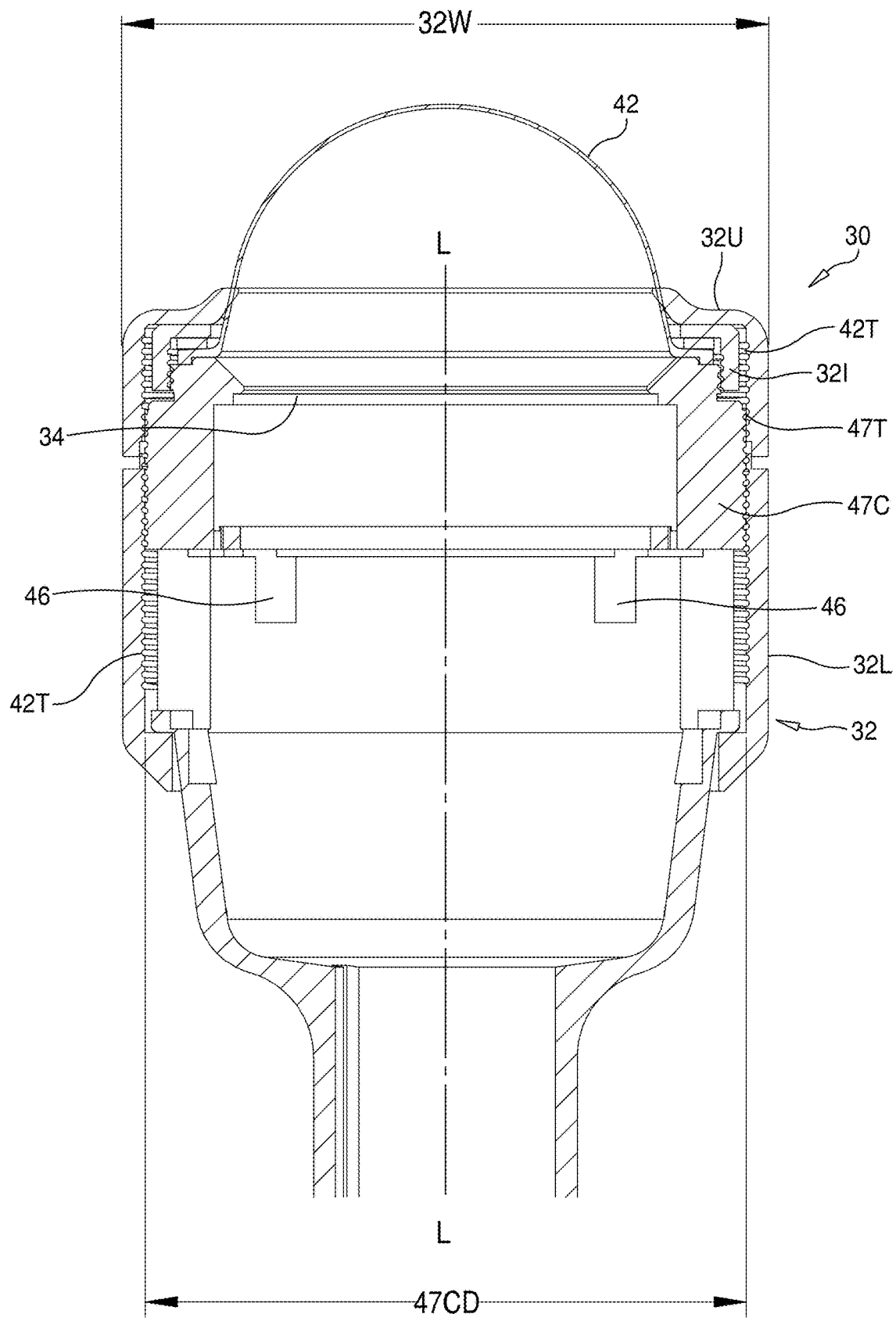
FIG. 3H is a longitudinal sectional view of the probe of FIG. 3F.

FIG. 3H is a longitudinal sectional view of probe 30, according to the embodiment shown in FIG. 3F. A lower housing part 32L joins the lower portion of the probe 30 that contains terminals 46 with the substrate and coil 34 via LEAP cap 47C. LEAP cap 47C has an outside dimension 47CD that is less than the outside dimension 32W of the housing 32U, 32L and is joined thereto by means of mating threading 47T, 42T. The outside dimension of LEAP cap 47C, typically an outside diameter, is typically less than or equal to about 122 mm, preferably less than or equal to about 107 mm, even more preferably, less than about 82 mm. In some embodiments, the outside dimension of LEAP cap 47C is less than or equal to 78 mm, and in some embodiments, is in the range from about 52 mm to about 72 mm. In one particular example as shown in FIG. 3B, the outside dimension (outside diameter) was about 70 mm. In another particular example, the outside diameter was about 66 mm.

An intermediate housing portion 321 mounts the driver 38 (not visible in FIG. 3H) and gasket 40 (not visible in FIG. 3H) to the portion that holds the coil 34 and an upper housing portion 32U mounts the flexible diaphragm 42 to the probe 30. Each housing portion is shown as being connected by mating threads 42T although other equivalent mechanisms for joining components could be alternatively used, as would be apparent to one of ordinary skill in the art. The housing components can be molded from plastic or 3-D printed for example, while the portions of the probe that the housing 42 is attached to are typically metallic, such as stainless steel or other compatible metal, but could be rigid composite, ceramic, or the like.

In the example shown in FIG. 3F, the length 30L of the probe 30 was 210 mm. In the example shown in FIG. 3B, the length 30L was 207 mm. However, length 30L may vary in a range from about 150 mm to about 250 mm, typically from about 175 mm to about 225 mm, from about 180 mm to about 220 mm, from about 185 mm to about 215 mm from about 190 mm to about 210 mm or any values therebetween. The width (outside diameter) 32W2 of the proximal end of the probe 30 in FIG. 3F was 36 mm, but this dimension may vary in a range from about 25 mm to about 50 mm, for example, 25 mm, 30 mm, 35 mm, 40 mm, 45 mm, 50 mm, or any other width value between 25 mm and 50 mm A connector assembly 49 may form a proximal end of the probe 30, as illustrated in FIGS. 3B and 3D.

Figure 4A:
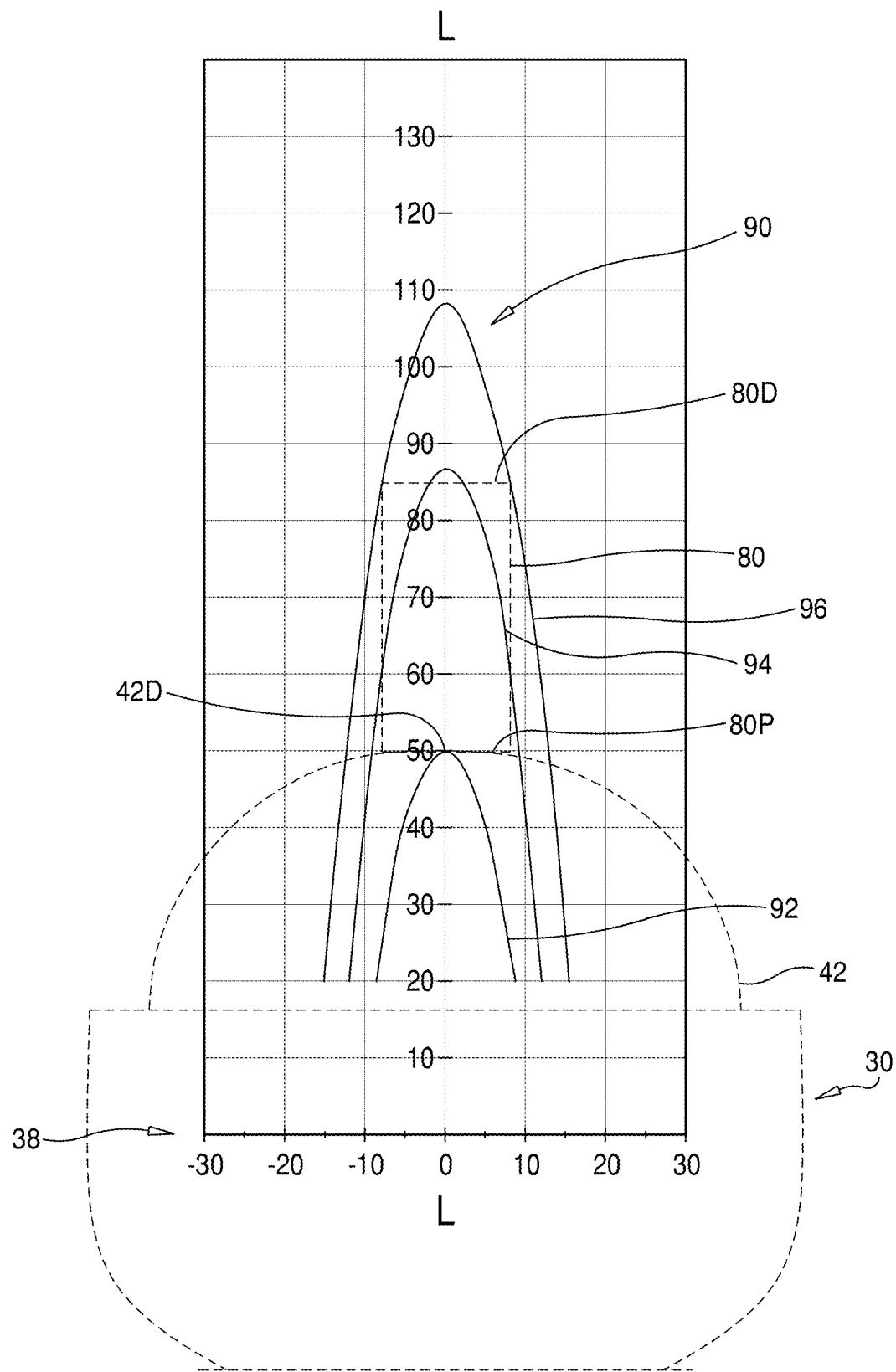
FIG. 4A is a schematic illustration of a probe emitting a low energy acoustic pulse according to an embodiment of the present invention.
Figure 4B:
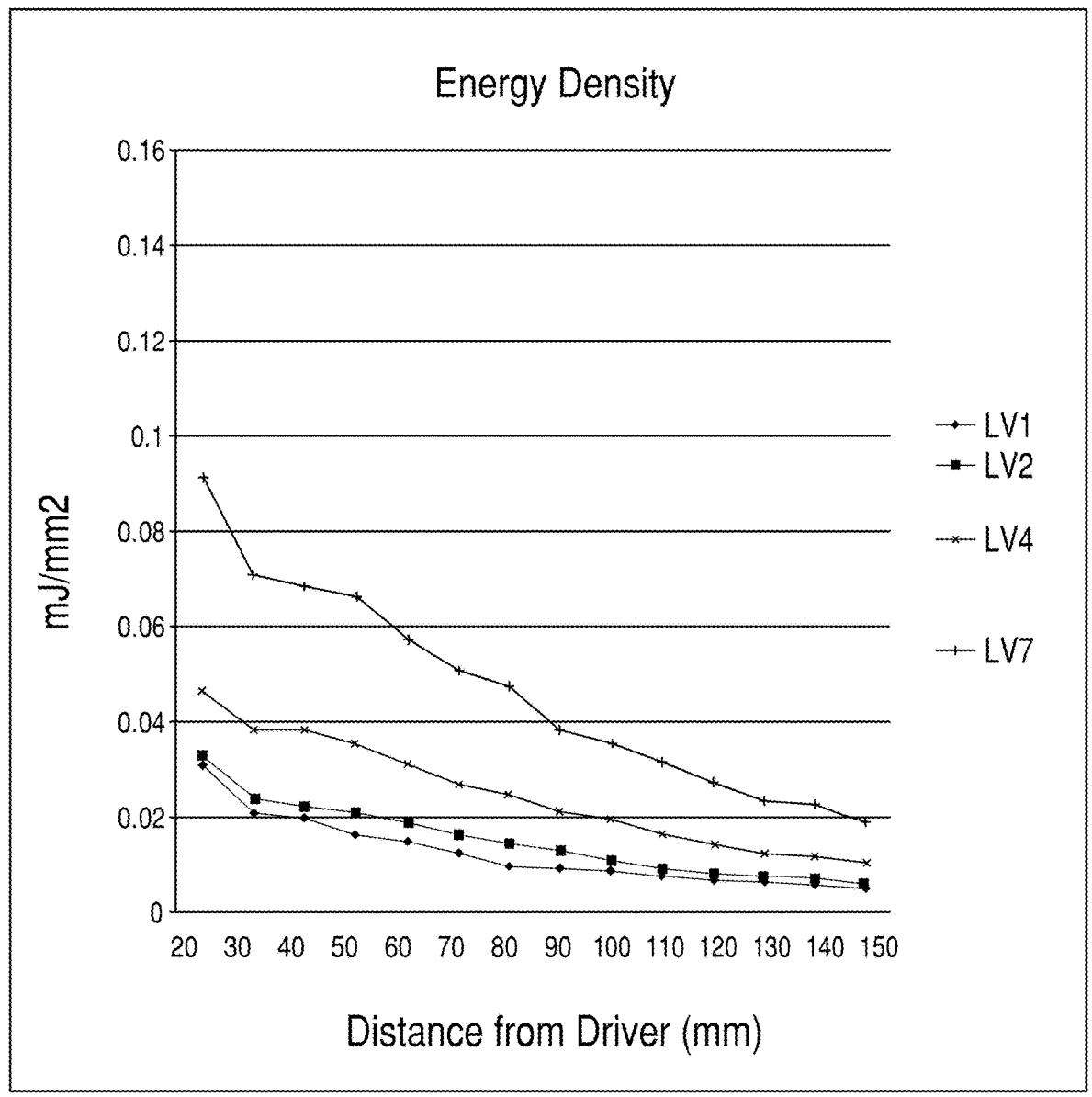
FIG. 4B illustrates energy density (along the central axis) for four different energy level settings according to an embodiment of the present invention.

FIG. 4A shows a diagram of the energy field 90 emitted by probe 30 according to an embodiment of the present invention shown in FIG. 3F-H. In the example shown, the voltage level was 8,500V and the flexible diaphragm 42 was extended 50 mm from the source of LEAP generation, as shown, with the location of the driver 38 being at 0 mm Thus location 42D is considered to be at the 100% energy density value for this diagram, wherein the energy density level is 0.035 mJ/mm$^2$. Because the energy field 90 is rotationally symmetric, the energy field 90 appears the same as that shown in FIGS. 4A, 4C (and all other FIGS. showing energy field diagrams) in all planes that include the longitudinal axis L-L of the probe 30/energy field 90. The energy density values decrease and never increase in a direction along the longitudinal axis L-L away from the source of generation of the LEAP, i.e., in the upward direction as shown in FIG. 4A. FIG. 4B illustrates this, showing energy density plots for four different energy level settings (LV1=8.0 kV, LV2=8.5 kV, LV4=9.5 kV and LV7=11.0 kV), illustrating the principle just described, by plotting energy density levels for these various settings along the longitudinal axis of the waveforms, starting from the origin, and moving outwardly along the X-axis. The Y-axis indicates the energy density values, in mJ/mm$^2$. For each level plotted, the energy density values decrease and never increase in a direction along the longitudinal axis L-L away from the source of generation of the LEAP (i.e., along the X-axis going from left to right).

Likewise, the energy density values decrease and never increase in directions normal to the longitudinal axis, in directions away from the longitudinal axis (e.g., in left and right directions shown in FIG. 4A (and all other FIGS. showing energy field diagrams), as well as all other directions radially extending 360 degrees about the longitudinal axis L-L), relative to the energy density value on the longitudinal axis L-L intersecting the line extending normally from L-L on which the energy density values are measured.

Envelope 92 connects energy density values equal to the 100% reference value of 0.035 mJ/mm$^2$ in this embodiment. Thus all locations below and within the envelope 92 have an energy density of 100% or greater of the maximum energy density value at 42D. Envelope 94 connects energy density values having 65% of the reference maximum energy density value generated by this embodiment. In this embodiment, the 65% of the reference maximum energy density value was 0.023 mJ/mm$^2$. Thus all locations below and within the envelope 94 have an energy density of 65% or greater of the maximum energy density value. Envelope 96 connects energy density values having 50% of the maximum energy density value generated by this embodiment. In this embodiment, the 50% of maximum energy density value was 0.0175 mJ/mm$^2$. Thus all locations below and within the envelope 96 have an energy density of 50% or greater of the maximum energy density value.

A cylinder 80 having a length of 35 mm and a diameter of 16 mm is shown superimposed on the energy field 90. As the cylinder 80 is contained within the energy density field 90, and because of the characteristics of the energy density field 90 described above, the limiting values defining an energy density of 50% or greater of the maximum energy density value (for envelope 96 shown, or for any percentage defined by any other envelope) are those at the top left and right corners of the distal end 80D of the cylinder 80. These values represent 50% of the maximum energy density value in this example, as they are located on the envelope 96. Of course, all locations circumferentially around the distal end 80D also have 50% of the maximum energy density value. The fact that the distal end values of the cylinder (distal corners of the rectangle that two-dimensionally represents the cylinder) are the limiting factors of the overall length of the cylinder is a function of the shape of the energy density field 90. The contours/envelopes of the energy density field 90 are wider at the base and get successively narrower with increasing distance away from the source of generation thereof.

All locations within or on cylinder 80 have an energy density that is at least 50% of the reference maximum energy density. Thus, all locations in or on the cylinder 80 in the example shown in FIG. 4A have an energy density value of at least 0.018 mJ/mm$^2$.

Because of the EFD characteristics of the cylinder 80 described above, additional cylinders (or any other three dimensional space within cylinder 80 and thus a subset of the volume of cylinder 80) can be defined within the space occupied by cylinder 80 that also have the characteristics as described for cylinder 80 above. That is, the energy density of any location on or within such subset volume of volume 80 (smaller cylinder or other smaller volume contained within cylinder 80) is at least 50% (−3 dB) of the reference 100% EFD at location 42D. For example, such a space or cylinder may be defined having a length of less than or equal to 35 mm (e.g., 30 mm to 35 mm, 25 mm to 30 mm, 20 mm to 25 mm, 15 mm to 20 mm, 10 mm to 15 mm, 5 mm to 10 mm, or 1 mm to 5 mm, or any length value within these ranges). For any and all of these lengths, the width can be 16 mm, 15 mm, 14 mm to 16 mm, 14 mm, 13 mm, 12 mm, 11 mm, 10 mm, 9 mm, 5 mm to 9 mm, 0.1 mm to 5 mm, or any width value between the stated values. For non-radially symmetrical spaces, the depth can be different from the width and can be 16 mm, 15 mm, 14 mm to 16 mm, 14 mm, 13 mm, 12 mm, 11 mm, 10 mm, 9 mm, 5 mm to 9 mm, 0.1 mm to 5 mm, or any width value between the stated values. These same principles apply generally to sub-volumes of any cylinder described herein with any reference maximum EFD defined.

Figure 4C:
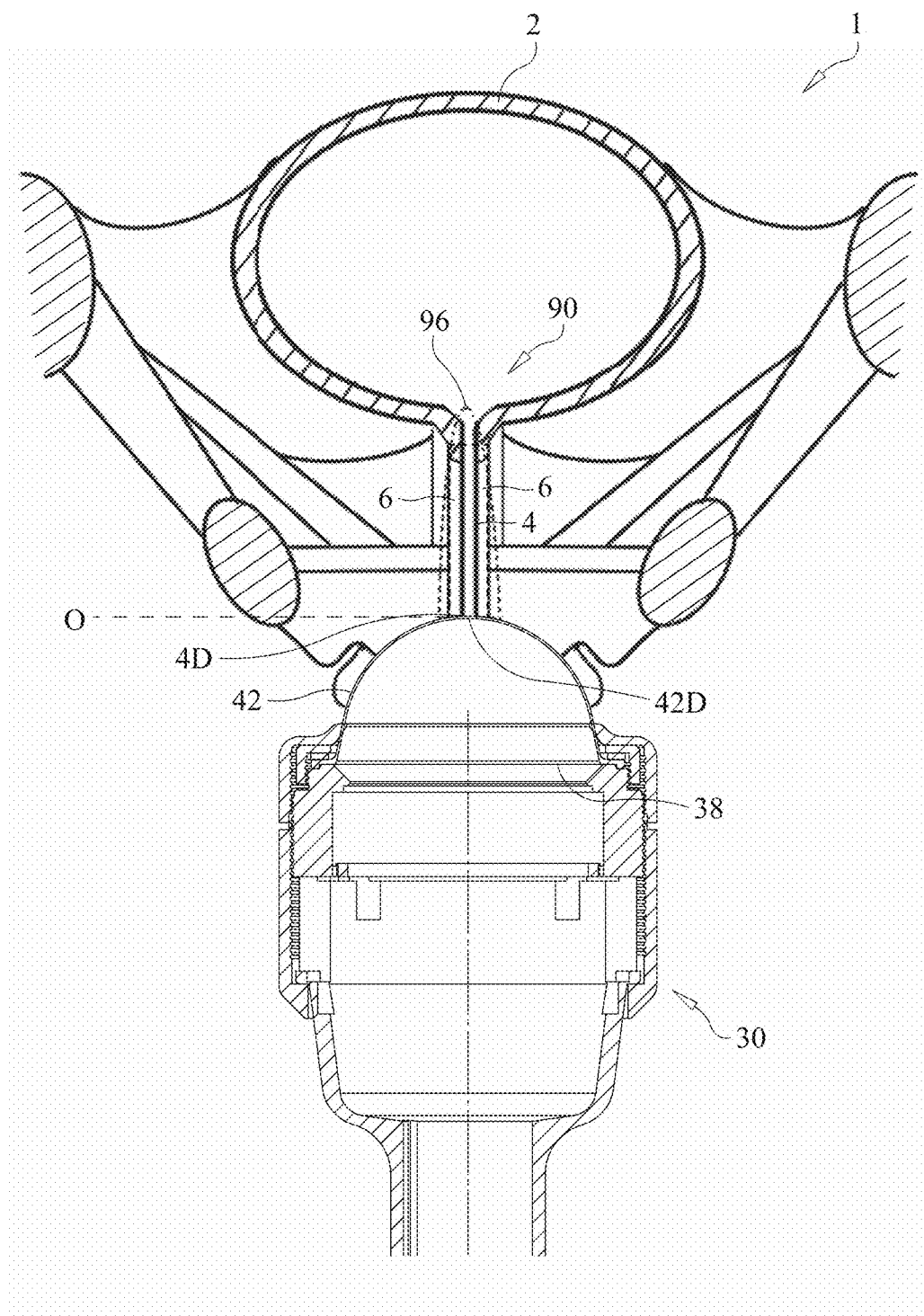
FIG. 4C illustrates, in a transverse plane, a diagram of the energy field emitted by the probe in the embodiment of FIG. 4A applied to a female patient, according to an embodiment of the present invention.

FIG. 4C is an illustration, in a transverse plane, of an application of a LEAP characterized by the energy field of FIG. 4A to an adult female patient for treatment of UI, according to an embodiment of the present invention. Probe 30 is positioned with flexible diaphragm 42 extended in a manner as described above, with flexible diaphragm 42 contacting the body of the patient 1, in contact with or adjacent to the distal end of the urethra 4. The distal end 42D of the flexible diaphragm may be positioned to contact the distal end 4D (urethral meatus) of the urethra 4, as shown in FIG. 4C, and the probe 30 is positioned between the legs of the patient 1.

The LEAP generating system 10 is then actuated to generate a LEAP 90 and deliver it into the body of the patient 1 in a direction along a length of the urethra 4. Typically this procedure is repeated at a predetermined frequency of application of LEAPs for a predetermined number of times. Since the urethra 4 and urethral sphincter muscles 6 are preferably treated only from the end of the urethra 4 in a lengthwise direction along the urethra 4 and urethral sphincter muscles, this simplifies the procedure relative to prior art techniques and provides superior results.

The LEAP 90 has an energy density field that is dimensioned to therapeutically encompass the urethra 4 and urethral sphincter muscles 6 of the patient 1, and is configured to provide a therapeutically effective level of energy density for treatment of the urethra 4 and urethral sphincter muscles 6 for UI.

The energy density field 90 is configured to provide a therapeutically effective treatment when applied in a direction along the longitudinal axis of the urethra 4. To accomplish this, at least 30% of the volume of the urethra 4 and urethral sphincter muscles 6, are simultaneously encompassed by energy density of the energy density field 90 having at least 50% of the reference maximum energy density located along a central axis of the energy density field at a location of the end of the urethra (i.e., location 4D shown in FIG. 4C). Preferably at least 40% of the volume of the urethra and urethral sphincter muscles are simultaneously encompassed, more preferably, at least 50%, or 60%, 70%, 80%, 90% or 99%.

Figure 4D:
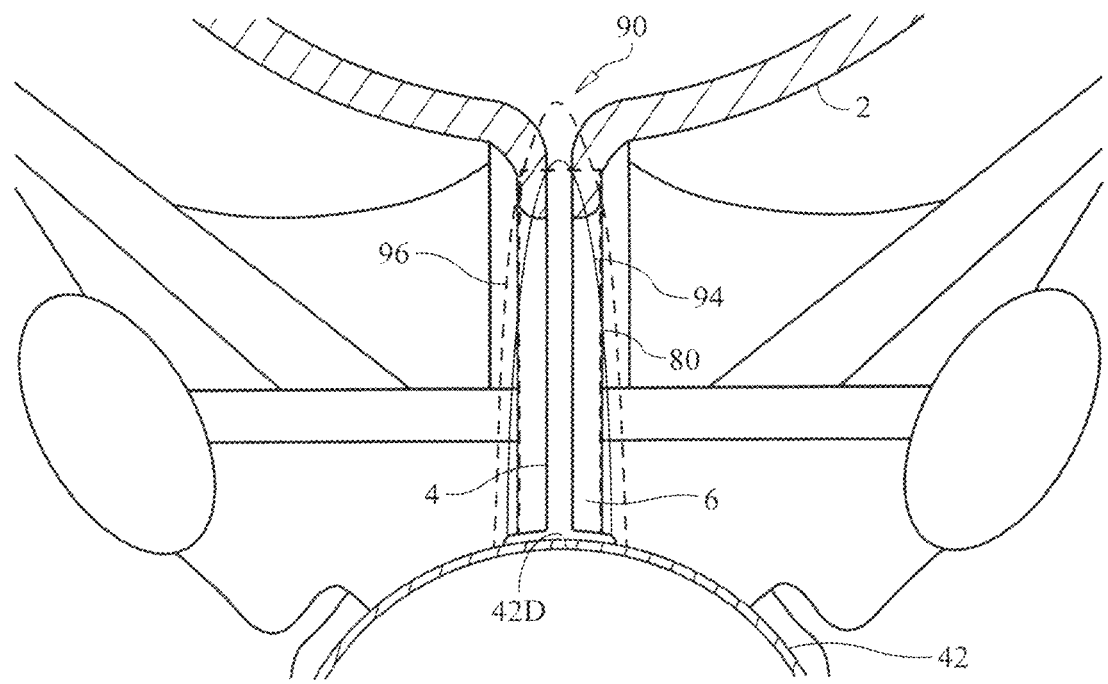
FIG. 4D is an enlarged, partial view of the schematic representation shown in FIG. 4C, additionally showing a cylinder superimposed on the energy density field.

FIG. 4D is an enlarged, partial view of the schematic representation shown in FIG. 4C, to additionally show cylinder 80 superimposed on the energy density field 90 as applied to the female anatomy and described with reference to FIG. 4C. FIG. 4D shows that the cylinder 80 simultaneously encompasses about 87.5% (cylinder length 35 mm divided by 40 mm urethra 4 and sphincters 6 length of 40 mm, wherein the full diameters of the urethra 4 and urethral sphincters 6 are encompassed over the full 35 mm length of the cylinder 80) of the urethra 4 and urethra sphincter muscles 6, wherein the cylinder 80 has a minimum EFD of 0.018 mJ/mm$^2$. Because the main urethral sphincter muscles 6 of the urethra 4 are located approximately at the middle of the length of the urethra 4, therapeutically effective treatments can be provided by any of the embodiments of probe 30 described above and throughout this disclosure.

Any percentage values in between the stated percentage values can also be obtained as the amount of urethral sphincter muscles 6 simultaneously encompassed by at least 50% of the maximum energy density of the field.

The maximum energy flux density (EFD) measured at 42D may be less than or equal to 0.175 mJ/mm$^2$, less than or equal to 0.16 mJ/mm$^2$, less than or equal to 0.158 mJ/mm$^2$, less than or equal to 0.15 mJ/mm$^2$, less than or equal to 0.14 mJ/mm$^2$, less than or equal to 0.123 mJ/mm$^2$, from 0.005 mj/mm$^2$ to 0.04 mJ/mm$^2$, from 0.008 mJ/mm$^2$ to 0.05 mJ/mm$^2$, from greater than 0.05 mJ/mm$^2$ to 0.07 mJ/mm$^2$, from greater than 0.04 mJ/mm$^2$ to 0.05 mJ/mm$^2$, from greater than 0.05 mJ/mm$^2$ to 0.08 mJ/mm$^2$, from greater than 0.08 mJ/mm$^2$ to 0.10 mJ/mm$^2$, from greater than 0.10 mJ/mm$^2$ to 0.12 mJ/mm$^2$, from greater than 0.12 mJ/mm$^2$ to 0.14 mJ/mm$^2$, from greater than 0.14 mJ/mm$^2$ to 0.16 mJ/mm$^2$, from greater than 0.16 mJ/mm$^2$ to 0.18 mJ/mm$^2$, from greater than 0.18 mJ/mm$^2$ to 0.20 mJ/mm$^2$, from 0.01 mJ/mm$^2$ to about 0.03 mJ/mm$^2$, from 0.02 mJ/mm$^2$ to about 0.06 mJ/mm$^2$, from 0.01 mJ/mm$^2$ to 0.02 mJ/mm$^2$, from 0.02 mJ/mm$^2$ to about 0.04 mJ/mm$^2$, or have any value between 0.005 mJ/mm$^2$ and 0.175 mJ/mm$^2$. Although the maximum EFD level may be any of the values described above, it is not recommended to use EFD levels of 0.12 mJ/mm$^2$ or higher for treatment of the female urethra, as such levels are generally considered to be too high to be tolerated by a patient being treated in the area of the female urethra.

Although the LEAP 90 and LEAP generating apparatus configuration described with regard to FIGS. 4A and 4C-4D is preferably for treatment of the female urethra, it can alternatively be used for any of the other treatments described herein.

Figure 4E:
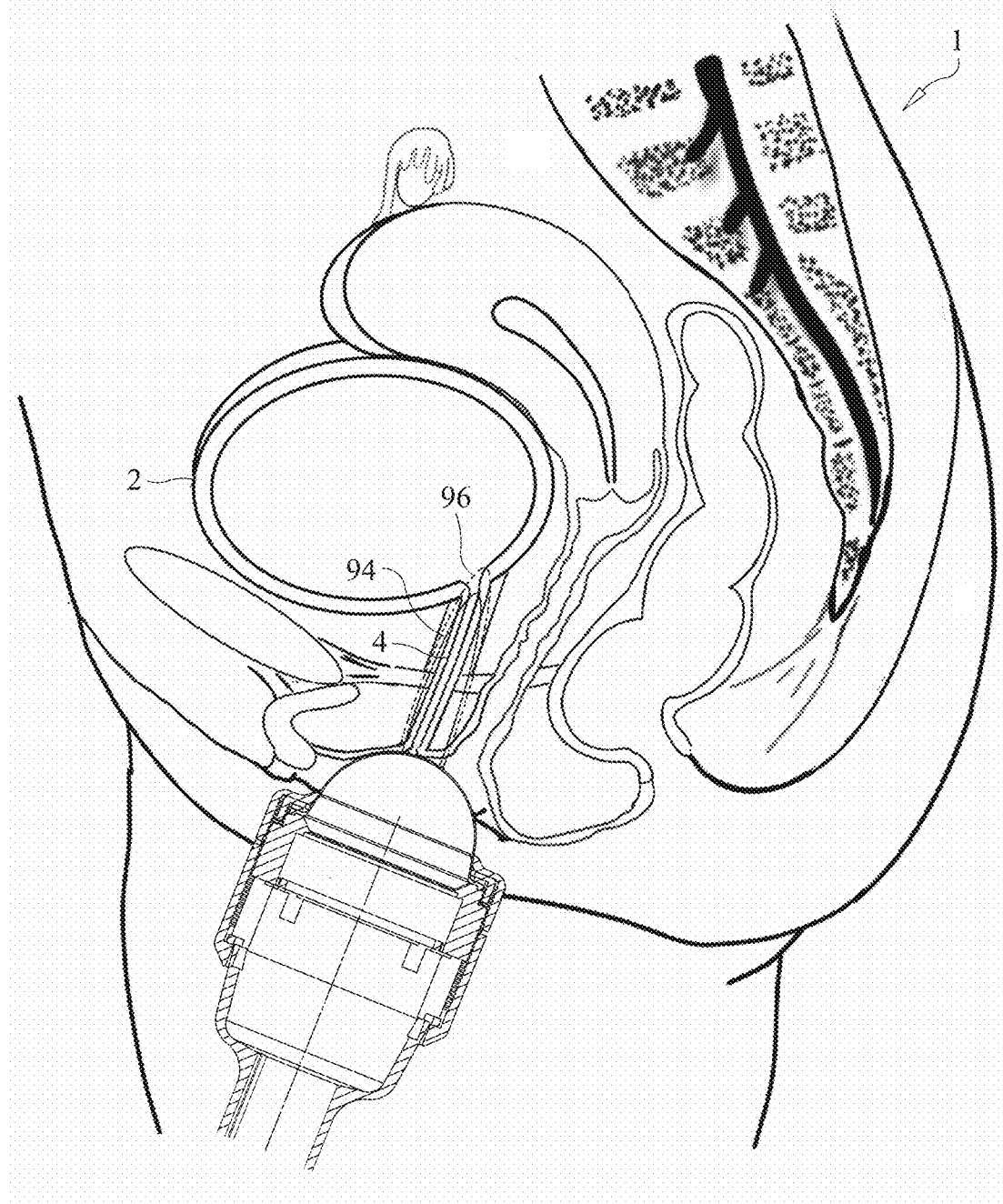
FIG. 4E is an illustration in the sagittal plane of the LEAP treatment of the patient illustrated in FIG. 4C.

At locations distal of the cylinder 80, the 50% envelope 96 narrows as the energy density levels decrease. The 50% envelope terminates about 22 mm distal of the cylinder 80 in FIGS. 4C-4E. After about 100 mm-110 mm from the driver 38, the energy density falls off significantly as illustrated in FIG. 4A. This is beneficial as it avoids treating or damaging tissues that are not target tissues. The average length and diameter of the adult female urethra 4, including the urethral sphincter muscles 6 are about 4 cm length and 16 mm diameter, respectively. The main sphincter muscles 6 are concentrated around about the middle third (lengthwise) of the urethra 4 with internal sphincter muscle 6 extending from smooth muscle of the bladder, over most of the length of the urethra 4, out to the open end of the urethra 4. Applying these values to FIGS. 4C-4D, it can be observed that none of the energy within the 65% envelope 94 (0.023 mJ/mm$^2$) is applied to organs such as the bladder 2, or any organs other than the urethra 4 and urethral sphincter muscles 6, while only a minimal portion of the 50% envelope 96 (0.018 mJ/mm$^2$) reaches the bladder 2. This is also shown in FIG. 4E, which is an illustration in the sagittal plane of the LEAP treatment of the patient illustrated in FIG. 4C. This is beneficial as it focuses the application of therapy on the desired target tissues, while the therapeutically effective levels of energy field density drop off quickly beyond the locations of the target tissues, to avoid treating other organs and tissues, thereby greatly reducing any risk of adversely affecting tissues/organs that are not the intended target. As noted, the bladder 2 receives almost none of the energy in envelope 96, so that only a significantly reduced energy density is applied beyond that. The colon is not exposed to any significant amount of energy and the uterus is exposed to very little energy, no more than 0.009 mJ/mm$^2$, and the ovaries and fallopian tubes are not exposed. By applying a LEAP of non-increasing intensity from a source at the opposite (distal) end of the urethra 4 and providing an energy field that applies the majority of energy to the therapeutic target area with a significant fall off of energy beyond the target area, the present invention provides a safe and effective alternative to known treatment methods. In this and all other embodiments described herein, the energy density levels that are disclosed are only particular examples of use of those embodiments, as energy density levels can be varied, such as by changing the amount of voltage applied to the system, by varying the distance by which the distal end of the flexible diaphragm 42 extends from the driver 38, etc. The maximum energy density is at the point of contact of the flexible diaphragm 42 to the patient (e.g., the end 42D of the urethra 42 in FIG. 4C, but could be other locations, such as penile, anal, perineal, other locations on the skin etc.)

For the embodiment shown in FIGS. 4A and 4C-4E, although the preferred EFD at end of the urethra 4 (location 42D) was 0.035 mJ/mm$^2$, a therapeutic range for treatment of an adult female urethra for urinary incontinence to achieve a therapeutic result may include EFD at 42D of 0.005 to 0.11 mJ/mm$^2$ or any subrange thereof, preferably 0.009 mJ/mm$^2$ to 0.09 mJ/mm$^2$, more preferably 0.005 mJ/mm$^2$ to 0.07 mJ/mm$^2$, still more preferably from 0.005 mJ/mm$^2$ to 0.07 mJ/mm$^2$, or from 0.008 mJ/mm$^2$ to 0.035 mJ/mm$^2$ or from 0.035 mJ/mm$^2$ to 0.07 mJ/mm$^2$, a frequency of 1 to 10 Hz, for a duration of 2 minutes to 20 minutes, a frequency in any subrange of 1 to 10 Hz, for a duration in any subrange of 2 minutes to 20 minutes, more preferably EFD of 0.014 mJ/mm$^2$ to 0.07 mJ/mm$^2$, a frequency of 2 to 8 Hz and a duration of 4 minutes to about 15 minutes, or EFD of 0.018 mJ/mm$^2$ to 0.05 mJ/mm$^2$, a frequency of 3 Hz to 5 Hz and a duration of 6 minutes to 14 minutes. In one specific, non-limiting embodiment, a treatment was applied at EFD of 0.035 mJ/mm$^2$, and a frequency of 3 Hz for 6 minutes, followed by EFD of 0.035 mJ/mm$^2$ at a frequency of 5 Hz for 4 min.

Figure 5:
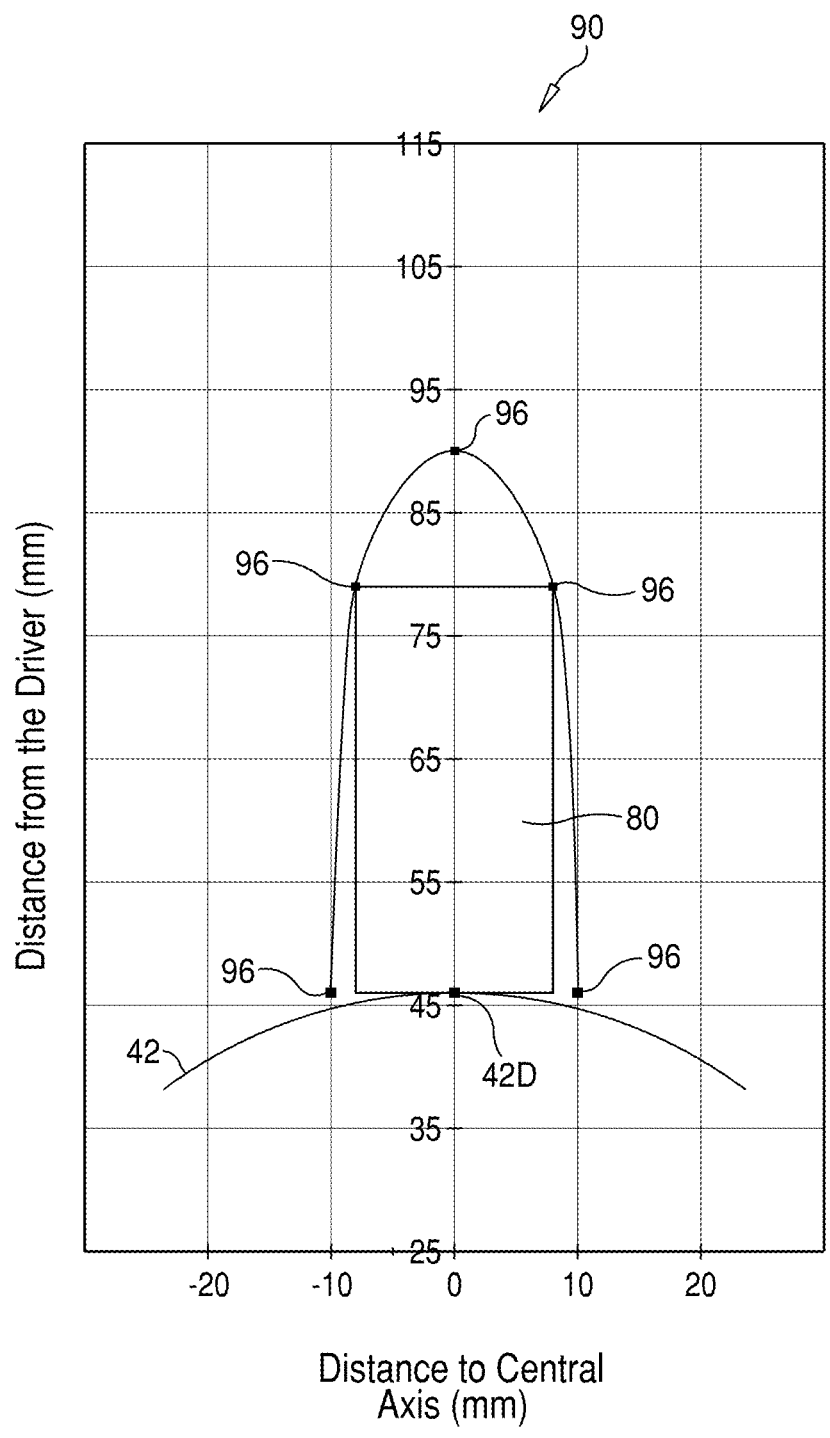
FIG. 5 shows a diagram of the energy field emitted by a probe according to an embodiment of the present invention.

FIG. 5 shows a diagram of an energy field 90 emitted by a probe 30 according to an embodiment of the present invention. In the example shown, the voltage level was 12,500V and the flexible diaphragm 42 was extended 46 mm from the source of LEAP generation, as shown, with the location of the driver 38 being at 0 mm Thus location 42D is considered to be at the 100% energy density value for this diagram, wherein the 100% energy density level is 0.123 mJ/mm$^2$ (maximum energy density value). For better clarity in viewing, only envelope 96 (the 50%) envelope is shown in FIG. 5.

Envelope 96 connects energy density values having 50% of the maximum energy density value generated by this embodiment. In this embodiment, the 50% of maximum energy density value was 0.061 mJ/mm$^2$. Thus all locations below and within the envelope 96 have an energy density of 50% or greater of the maximum energy density value.

Cylinder 80 in FIG. 5 has a length of 33 mm and a width (diameter) of 16 mm. As in previous embodiments, the energy density in the cylinder is at the minimum (50% of max EFD in this instance, 0.061 mJ/mm$^2$) at the top left and right corners of the rectangle 80 as shown in FIG. 5.

Figure 6:
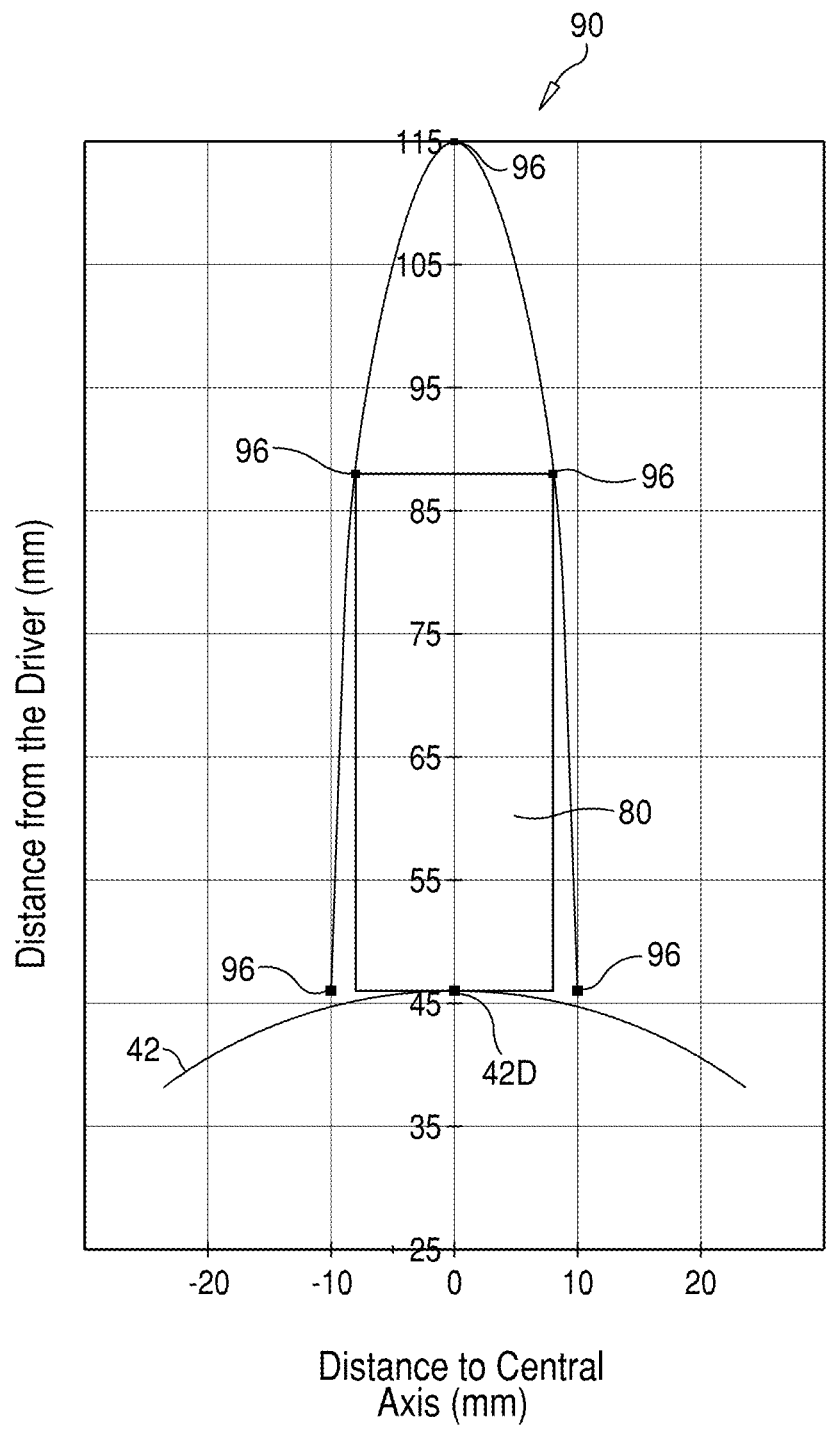
FIG. 6 shows a diagram of the energy field emitted by a probe according to an embodiment of the present invention.

FIG. 6 shows a shows a diagram of an energy field 90 emitted by a probe 30 according to an embodiment of the present invention. In the example shown, the voltage level was 7,000V and the flexible diaphragm 42 was extended 46 mm from the source of LEAP generation, as shown, with the location of the driver 38 being at 0 mm Thus location 42D is considered to be at the 100% energy density value for this diagram, wherein the 100% energy density level is 0.018 mJ/mm$^2$ (maximum energy density value). For better clarity in viewing, only envelope 96 (the 50%) envelope is shown in FIG. 6.

Envelope 96 connects energy density values having 50% of the maximum energy density value generated by this embodiment. In this embodiment, the 50% of maximum energy density value was 0.009 mJ/mm$^2$. Thus all locations below and within the envelope 96 have an energy density of 50% or greater of the maximum energy density value.

Cylinder 80 in FIG. 6 has a length of 42 mm and a width (diameter) of 16 mm. As in previous embodiments, the energy density in the cylinder 80 is at the minimum (50% of max EFD in this instance, 0.009 mJ/mm$^2$) at the top left and right corners of the rectangle 80 as shown in FIG. 6.

Figure 7:
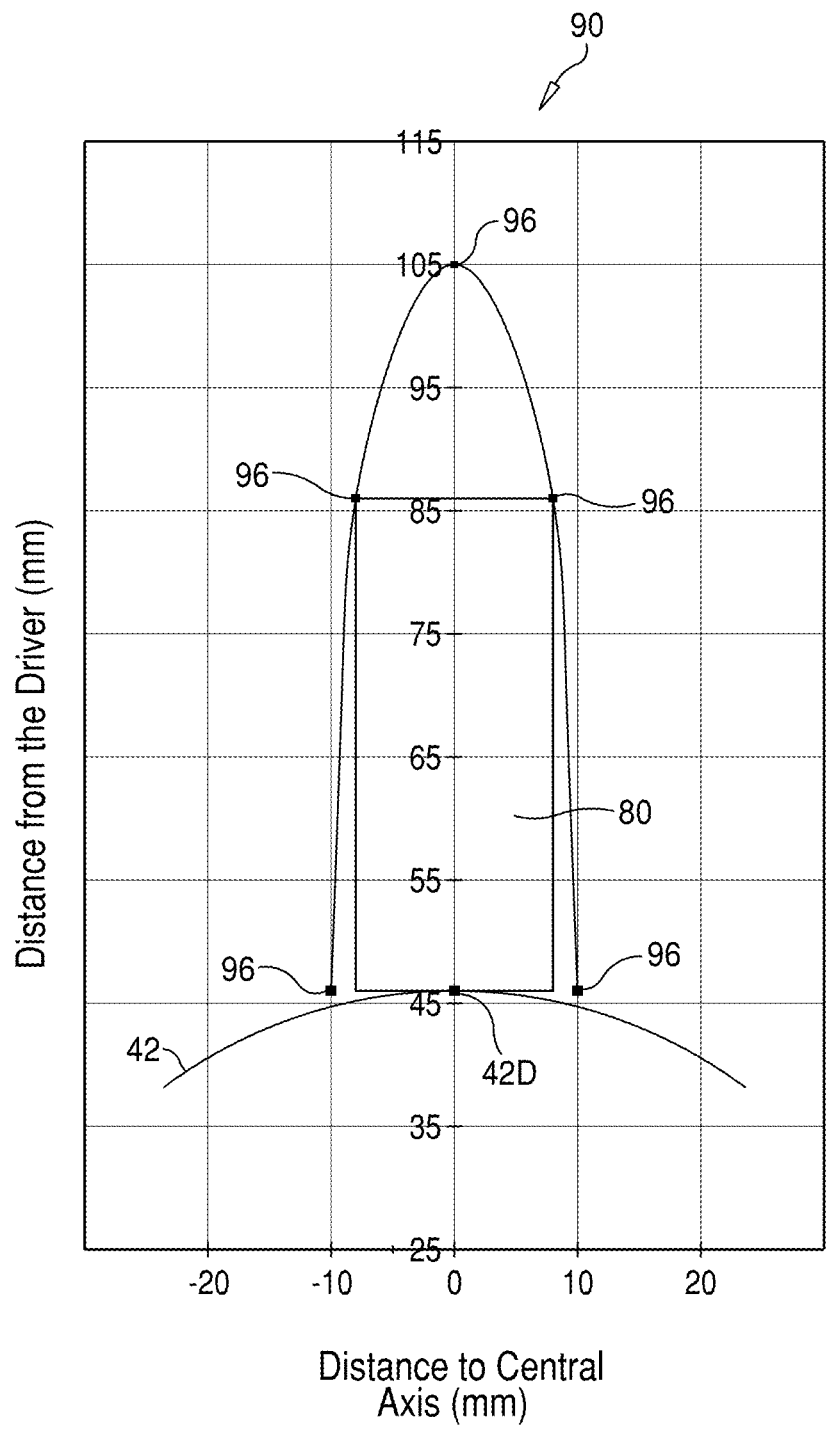
FIG. 7 shows a diagram of the energy field emitted by a probe according to an embodiment of the present invention.

FIG. 7 shows a diagram of an energy field 90 emitted by a probe 30 according to an embodiment of the present invention. In the example shown, the voltage level was 8,500V and the flexible diaphragm 42 was extended 46 mm from the source of shockwave generation, as shown, with the location of the driver 38 being at 0 mm Thus location 42D is considered to be at the 100% energy density value for this diagram, wherein the 100% energy density level is 0.035 mJ/mm$^2$ (maximum energy density value). For better clarity in viewing, only envelope 96 (the 50%) envelope is shown in FIG. 7.

Envelope 96 connects energy density values having 50% of the maximum energy density value generated by this embodiment. In this embodiment, the 50% of maximum energy density value was 0.018 mJ/mm$^2$. Thus all locations below and within the envelope 96 have an energy density of 50% or greater of the maximum energy density value.

Cylinder 80 in FIG. 7 has a length of 40 mm and a width (diameter) of 16 mm. As in previous embodiments, the energy density in the cylinder 80 is at the minimum (50% of max EFD in this instance, 0.018 mJ/mm$^2$) at the top left and right corners of the rectangle 80 as shown in FIG. 7.

Figure 8:
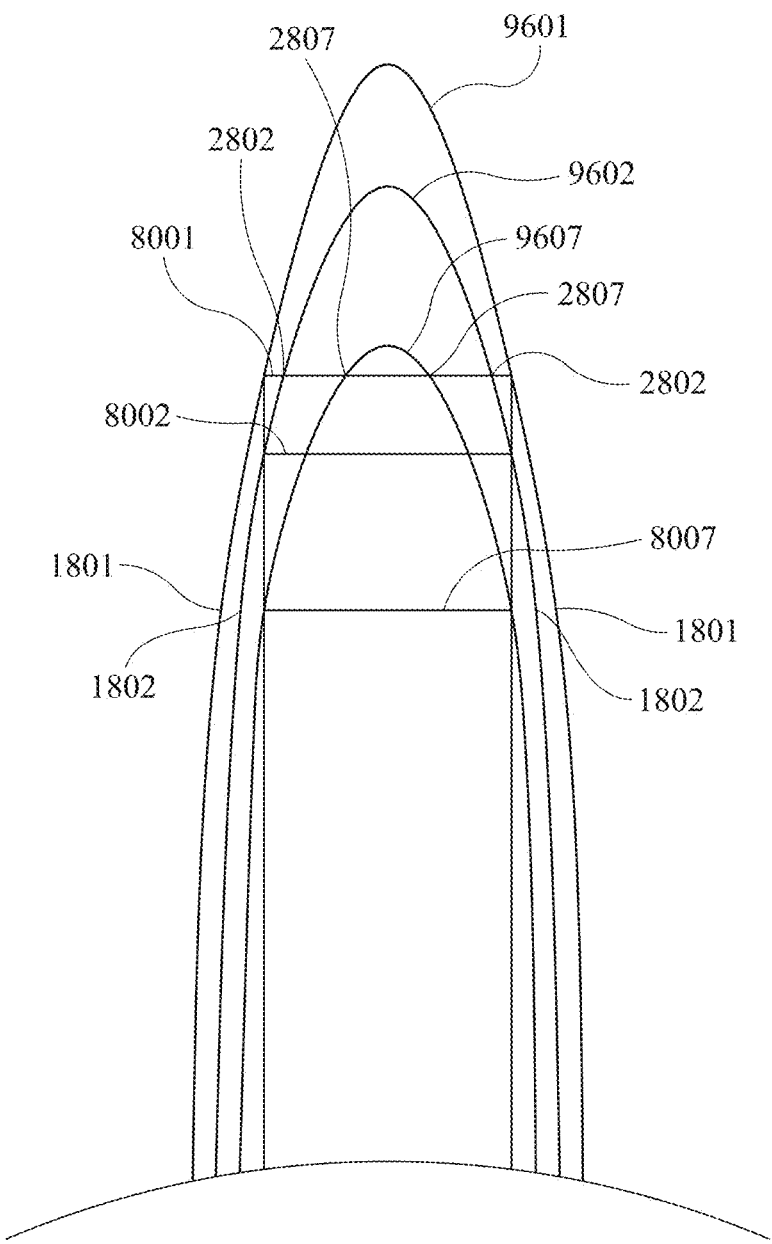
FIG. 8 illustrates an overlay of the 50% envelopes and cylinders of FIGS. 5-7.

FIG. 8 illustrates an overlay of the 50% envelopes and cylinders of FIGS. 5-7. The envelopes in FIG. 8 have not been drawn to scale, but have been exaggerated somewhat to show the nested relationship among them, with the spacing between them exaggerated for easier and more clear viewing to show the relative broadening and lengthening of the 50% envelopes as the 100% energy density level decreases. For clear identification, the 50% envelopes 96 of FIGS. 5-7 have been labeled 9607, 9601 and 9602 respectively referring to the 100% energy density levels of 0.123 mJ/mm$^2$, 0.018 mJ/mm$^2$ and 0.035 mJ/mm$^2$ that they are measured against. Likewise, for clarity, the cylinders 80 have been labeled 8007, 8001 and 8002, respectively referring to the 0.123 mJ/mm$^2$, 0.018 mJ/mm$^2$ and 0.035 mJ/mm$^2$ examples of FIGS. 5, 6 and 7. For any given cylinder length the diameter thereof advantageously increases as the 100% energy level decreases, where the diameter is measured between opposing distal end points of the cylinder that intersect with the 50% envelope. For example, for the cylinder 8007 having a length of 33 mm, the diameter (width, as shown two-dimensionally in the figures) when the 100% energy level is 0.123 mJ/mm$^2$ is 16 mm as already described with regard to FIG. 5. At the same length, a cylinder can be defined including points 1802 that has a diameter greater than 16 mm (about 17 mm) for the 50% EFD envelope 9602 (when the 100% energy level is 0.035 mJ/mm$^2$) and a cylinder can be defined including points 1801 that has a diameter greater than that of the cylinder defined by the 1802 points (about 18 mm) for the 50% EFD envelope 9601 (when the 100% energy level is 0.018 mJ/mm$^2$). As another example, for the cylinder 8001 having a length of 42 mm, the diameter (width, as shown two-dimensionally in the figures) when the 100% energy level is 0.018 mJ/mm$^2$ is 16 mm as already described with regard to FIG. 6. At the same length, a cylinder can be defined including points 2802 that has a diameter less than 16 mm (about 15 mm) for the 50% EFD envelope 9602 (when the 100% energy level is 0.035 mJ/mm$^2$) and a cylinder can be defined including points 2807 that has a diameter less than that of the cylinder defined by the 2802 points, about 10 mm for the 50% EFD envelope 9607 (when the 100% energy level is 0.123 mJ/mm$^2$).

This provides a distinct advantage over prior art devices that typically decrease the cylinder size within the 50% zone as the 100% energy level decreases, because the present invention can capture larger cylindrical volumes of tissue in the 50% (−3 dB) zone as the power levels decrease respectively. For sensitive soft tissues in general and particularly for treatment of the female urethra and urethral sphincter muscles as described herein, this is greatly advantageous for providing a large enough treatment zone (cylinder) to capture a sufficient volume of the soft tissues/urethral sphincter muscles at a low enough energy density level to be tolerated by the patient while still providing a therapeutic result. For treatment of the female urethra and urethral sphincter muscles, 100% energy levels up to 0.035 mJ/mm$^2$ have been found to be tolerable by patients, with 100% energy levels up to 0.05 mJ/mm$^2$ being possible, but difficult and where 100% energy levels of 0.07 mJ/mm$^2$ generally considered not clinically acceptable.

Figure 9:
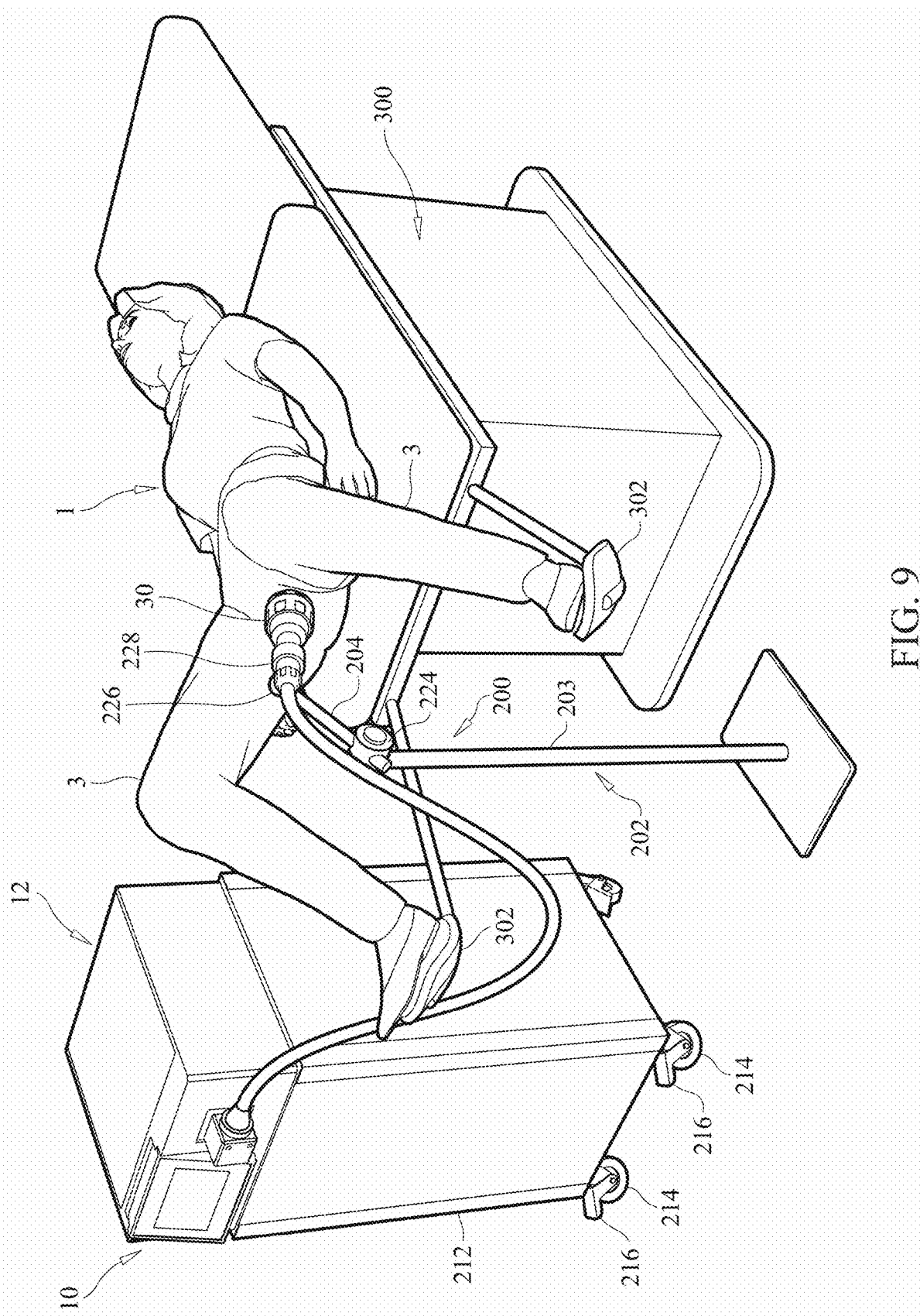
FIG. 9 shows a LEAP system in combination with a stabilizing system according to an embodiment of the present invention.

FIG. 9 shows the system 10 in combination with a stabilizing system 200, according to an embodiment of the present invention. The stabilizing system 200 includes a free standing mounting stand 202 having an adjustable arm 204 configured to allow probe 30 to be attached thereto. A cart 212 having wheels 214 and brakes 216 may be provided for supporting the control unit 12, whereby the cart 212 and control unit 12 can be moved to a desired treatment location and brakes 216 can be applied to fix the control unit 12 in the desired location adjacent the mounting stand 202. Alternatively, the control unit 212 could be supported by a table (not shown) or other relatively stationary support adjacent the mounting stand 202.

By fixing the probe 30 to the adjustable arm and fixing the adjustable arm 204 relative to the stationary stand 202, the probe 30 can be maintained in a stable position relative to the patient 1 during a procedure. FIG. 9 shows the cart 212 having been parked adjacent to a treatment table 300, and the brakes 216 have been applied to maintain the cart 212 in a fixed position relative to the treatment table 300 which is also maintained in position. The free-standing mounting stand 202 has been positioned between the stirrups 302 extending from the treatment table 300 so as to position the probe 30 in an appropriate location between the legs 3 of the patient 1 where it can be contacted to the patient's urethra 4 by insertion between the labia as described previously.

The probe is fixedly mounted to a probe holder 228 and free-standing mounting stand 202 includes adjustable clamping mechanisms 224 and 226 that, together with rotation of the stand 202, allow three degrees of adjustment of the positioning of the probe 30 when fixed in the probe holder 228. Height adjustments of the mechanical arm 204/probe 30 can also be made when clamping mechanism 224 is in the unlocked configuration, by sliding the clamping mechanism 224 up or down along the shaft 203 of the stand 202. Once properly adjusted as desired, the clamping mechanism 224 can be locked to prevent further rotation about this axis and to prevent sliding of the clamping mechanism 224 relative to the shaft 203. Clamping mechanism 226 allows rotation of the probe 30 relative to the connecting arm 204 about the longitudinal axis of the connecting arm 204. The probe 30 can also be brought nearer or further away from the patient 1/table 300, by sliding the connecting arm 204 axially relative to the clamping mechanism 224, sliding the clamping mechanism 226 relative to the connecting arm 204, and/or sliding the stand 202 relative to the table 300. Once properly adjusted as desired, the clamping mechanism 224 can be locked to prevent further rotation about this axis and to prevent sliding of the connecting arm 204.

Figure 11:
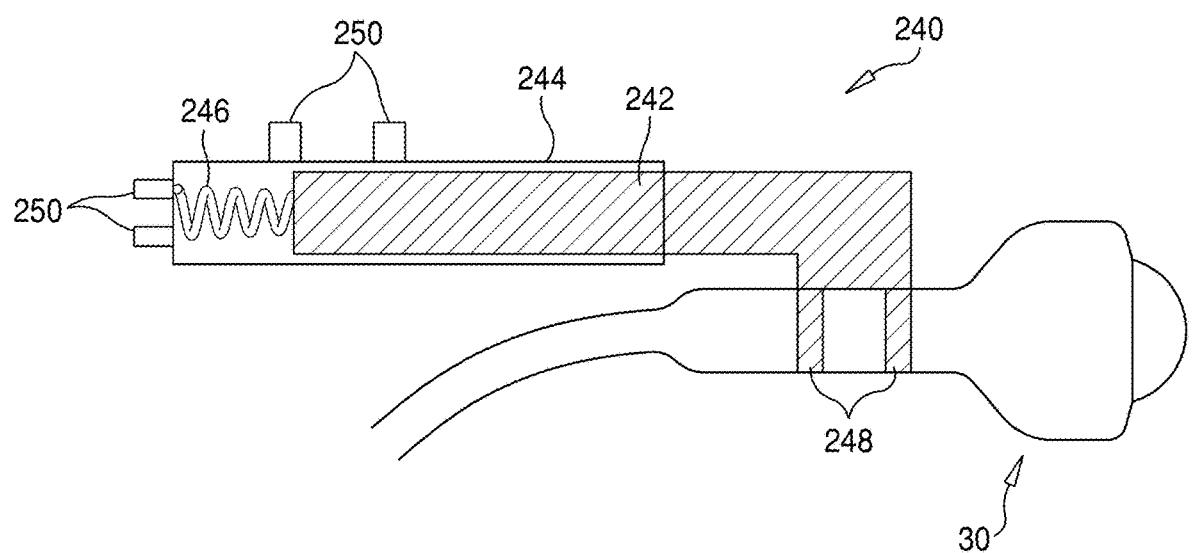
FIG. 11 illustrates a stabilizing mechanism according to an embodiment of the present invention.

A stabilizing mechanism 240 can optionally be provided to maintain the probe 30 (specifically, the flexible diaphragm 42 in contact with the urethra 4 in a relatively fixed position during the entirety of a procedure performed on the patient. FIG. 11 illustrates a stabilizing mechanism 240 according to one embodiment of the present invention that can optionally be used to assist in maintaining the probe 30 in contact with a patient with a desired amount of force so as to maintain a desired location and orientation of contact. The stabilizing mechanism 240 of FIG. 11 includes a piston 242 configured to slide within a cylinder 244. A biasing member 246 such as a coil spring or other resilient member is provided between a closed end of the cylinder 244 and the piston 242 so as to apply a counterforce to the piston 242 when the piston 242 is driven against the biasing member 246. Optionally, the biasing member 246 may be adjustable to adjust an amount of counterforce applied to the piston 242 at any predetermined location of the piston 242 relative the cylinder 244 as the piston is slid there within.

A mounting feature 248 such as clampable straps, bolts, screws or other equivalent attachment means are provided to mount the probe 30 to the stabilizing mechanism (specifically, to the piston 242 in the embodiment shown in FIG. 11) so as to prevent the probe 30 from being able to translate relative to the movable portion (e.g., piston 242) of the stabilizing mechanism. The stabilizing mechanism 240 is further provided with one or more bolts, studs, screws, clamps or other equivalent attachment means 250 configured to securely mount the stabilizing mechanism 240 to the probe holder 228 or other feature of the stabilizing system 200, 400 or 500. FIG. 11 shows alternate locations of attachment means 250 that may be located extending from the end of the stabilizing mechanism (e.g., extending from the closed end of the cylinder 244) or along the length of the cylinder 244.

By fixedly mounting the stabilizing mechanism 240 to the stabilizing system 200 or 400 and locking all adjustable joints of the stabilizing system 200 or 400, this fixes the cylinder 244 relative to the patient. The probe 30 is fixed relative to the piston 242, but can translate relative to the cylinder 244 along with the translation of the piston 242. The travel of the piston 242 within the cylinder is limited to a predefined distance which may be in the range of about 10 mm to about 100 mm, or 15 mm to 85 mm or 20 mm to 50 mm. In one particular embodiment, the travel limit was 30 mm.

The components of the stabilizing mechanism may be made from hollow or solid steel, aluminum, plastic or other material machined for smooth sliding action. The cylinder 244 and piston 242 have mating cross-sections to allow smooth sliding and for example, may be circular, rectangular, elliptical, oval or other polygonal cross-sectional shapes. The diameter (or largest cross-sectional dimension, for non-circular cross sections) of the cylinder 244 may be in a range from about 10 mm to 60 mm, typically from about 20 mm to about 50 mm, more typically from about 25 mm to about 35 mm. The length of the cylinder may be in a range from about 5 cm to about 20 cm, typically from about 10 cm to about 15 cm, and, in one embodiment was about 13 cm.

It is noted that although FIG. 11 and the description above refer to one specific embodiment of stabilizing mechanism, the present invention is not limited to this specific embodiment, as alternative stabilizing mechanisms configured to attach to a probe 30 and function to maintain the probe 30 with a predetermined amount of force could be used, including, but not limited to pneumatic, hydraulic, electromechanical, such as motor-driven with force feedback monitoring, or the like.

In use, the diaphragm 42 is contacted to the distal end 4D of the urethra 4 at a desired location and orientation. The clamping mechanisms 224 and 226 are placed into locking configurations to maintain the orientation of the probe 30 with the flexible diaphragm 42 in contact with the distal end 4D of the urethra as desired. Prior to contacting the diaphragm 42 to the patient, the probe 30/piston 242 are pushed relative to the cylinder 244 so that the piston 242 reaches the end of its travel and is held there. The diaphragm 42 is then contacted to the patient at the target location, and the user releases the hold on the piston 242 whereby the biasing member 246 applies a predetermined amount of force against the piston 242 which also maintains the predetermined amount of force through the diaphragm against the patient. The stabilizing mechanisms may be configured so that the predetermined amount of force applied by the probe 30/diaphragm 42 to the tissue of the patient is in the range of 0.1 to 5 pounds force (lbf), typically from about 0.5 to 3 lbf. In one particular embodiment, the predetermined amount of force that is maintained was about 1 lbf. By maintaining a predetermined amount of force to the probe 30 against the urethra 4, this ensures secure contact and proper orientation of the probe 30 relative to the target all throughout the procedure.

Figure 10:
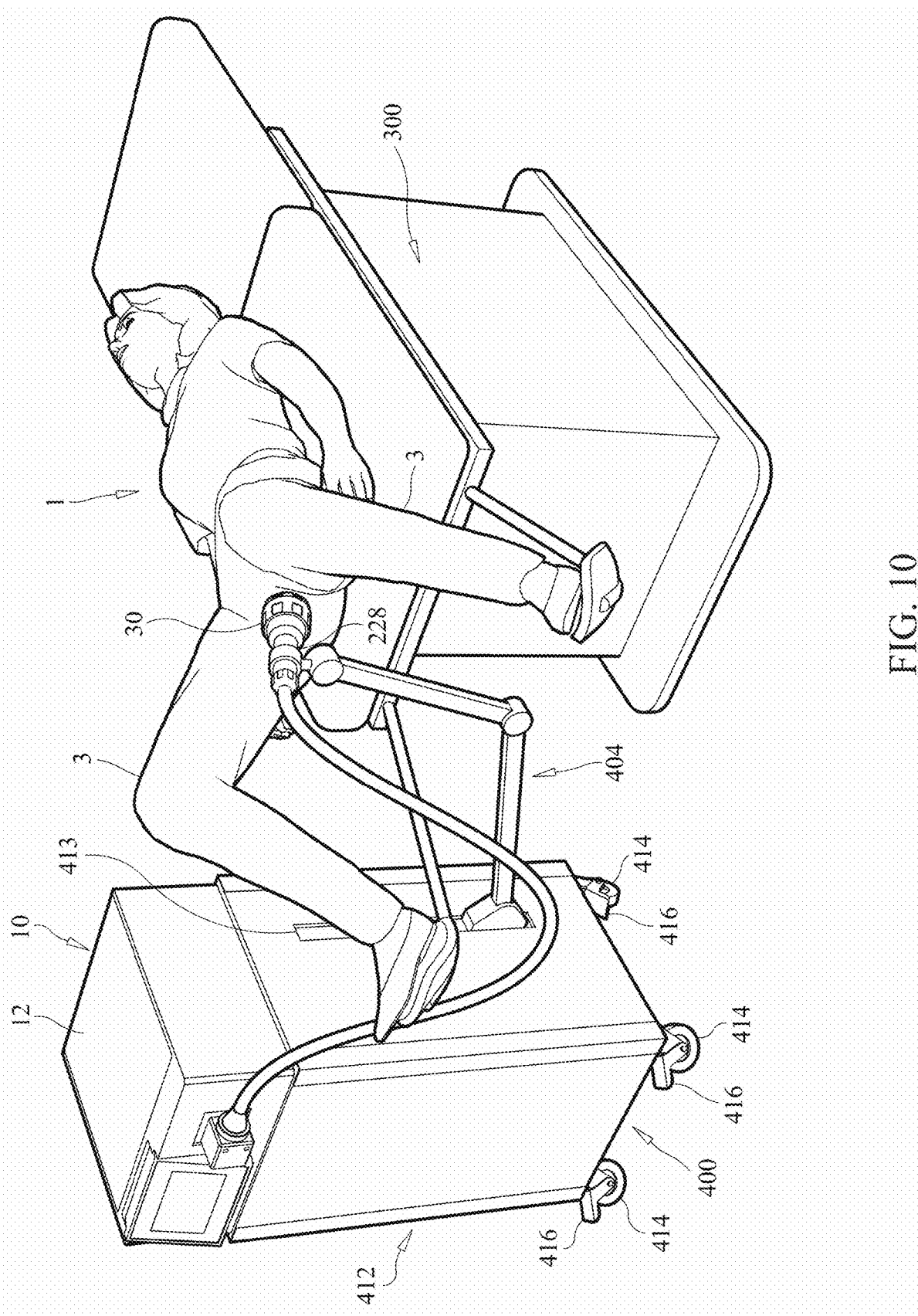
FIG. 10 shows a LEAP system in which a mounting arm is integrated into a cart, according to an embodiment of the present invention.

FIG. 10 shows the system 10 in combination with a stabilizing system 400, according to an embodiment of the present invention. The stabilizing system 400 includes an integrated mounting arm 404 configured to allow probe 30 to be attached thereto. Mounting arm 404 is integrated into a cart 412 such that mounting arm 404 can slide in a track 413 to allow height adjustments of the arm 404 relative to the table 300. Cart 412 includes wheels 414 and brakes 416 and can be further used to support the control unit 12, as shown, whereby the cart 412 and control unit 12 can be moved to a desired treatment location and brakes 416 can be applied to fix the control unit 12 in the desired location adjacent the treatment table 300 to allow the probe 30 to be appropriately positioned between the legs 3 of the patient 1 and in contact with or adjacent the end of the urethra. Alternatively, the control unit 12 could be supported by a table (not shown) or other relatively stationary support adjacent the cart 412.

By fixing the probe 30 to the adjustable arm 404 and fixing the adjustable arm 404 relative to the cart 412, the probe 30 can be maintained in a stable position relative to the patient 1 during a procedure. FIG. 10 shows the cart 412 having been parked adjacent a treatment table 300, and the brakes 416 have been applied to maintain the cart 412 in a fixed position relative to the treatment table 300 which is also maintained in position. The arm 404 is manipulated so as to position the probe 30 between the legs 3 of a patient 1 supported by the table 300, in contact with or adjacent to the end of the patient's urethra in a manner as described previously.

The probe 30 is fixedly received in a probe holder 228 (which can be locked for fixation, and unlocked to allow axial sliding and/or rotation of the probe 30 relative to probe holder 228) and the arm 404 functions in the same manner as arm 204 with the exception that linear height adjustment is along the track 413, rather than along a shaft 203 of a free-standing mounting stand 202. Otherwise, all adjustable clamping mechanisms and stabilizing mechanism are provided that function in the same way as that described with regard to the embodiment of FIG. 9. Either of the embodiments of FIGS. 9-10 can be modified. For example, the system 10 may be fully integrated into a stabilizing system according to an embodiment of the present invention, in which a mounting arm and control unit may be integrated into a cart. In any of these embodiments, probe 30 can be connected via a locking ball joint, or other clamping mechanism that allows it to be adjusted relative to the arm and then locked in a desired position and orientation relative to the arm.

In all of the embodiments described, adjustments can be made to position the probe 30, but once all adjustable features (e.g., clamping mechanisms) have been locked to position and orient the probe 30 as desired, the probe 30 is stationary relative to the patient during use unless intentionally moved by the operator.

Figure 12:
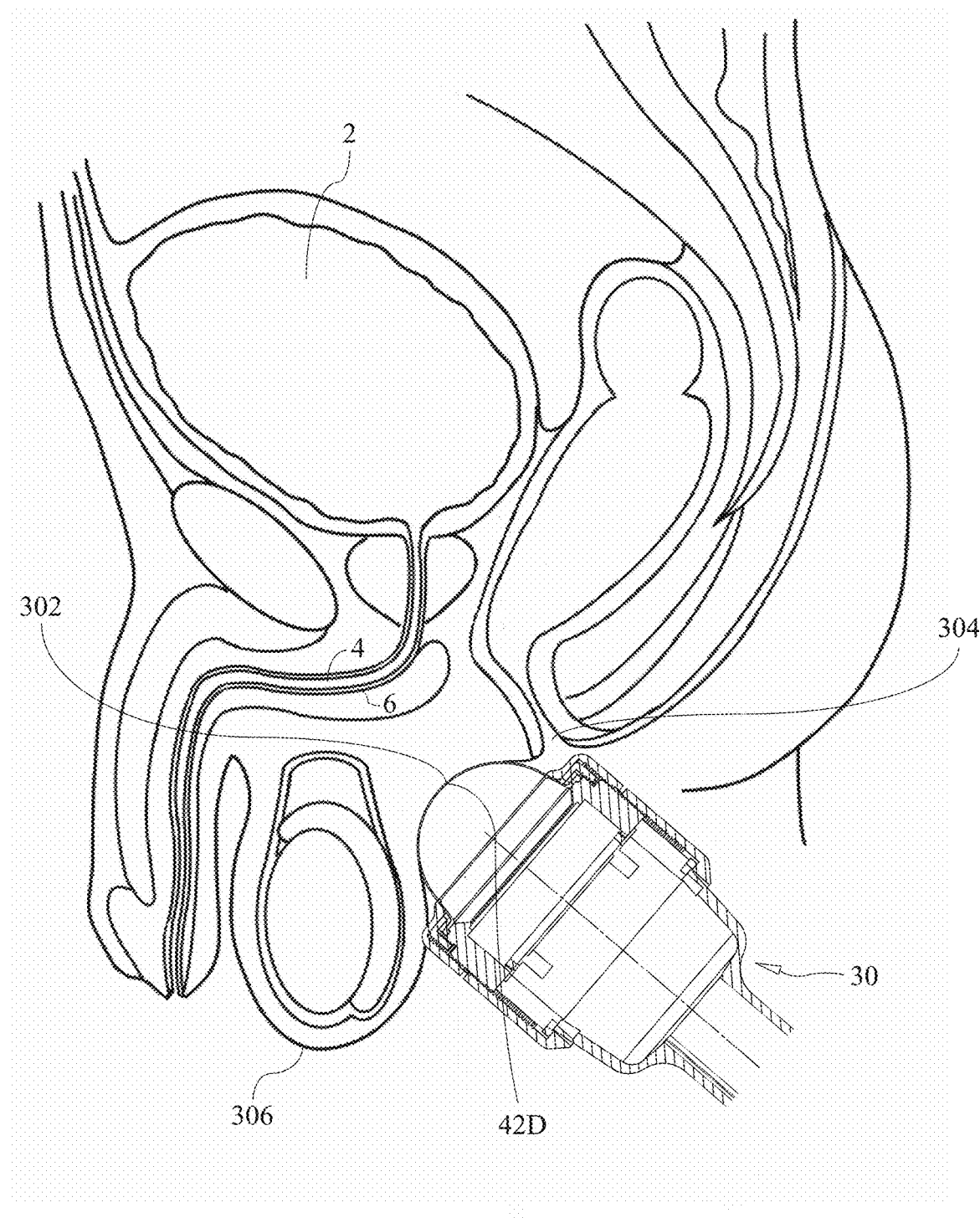
FIG. 12 illustrates perineal application of a probe to a male patient to treat urinary incontinence, according to an embodiment of the present invention.

In an alternative embodiment the system 10 can be applied to the perineum of a male patient to treat urinary incontinence. In this case the perineum 302 is the area between the anus 304 and the scrotum 306 of the male patient, see FIG. 12. In the case of a male patient, the urethra 4 and urethral sphincter muscles 6 are located about 3-6 cm in from the perineum 302. Accordingly, a higher power setting, relative to what is selected for treatment of the female urethra intra-labially, is selected on system 10 in order to provide a therapeutic range that extends the further distance to envelope the male urethra. For example, the maximum energy density value applied at location 42D may be about 0.105 mJ/mm$^2$ and about 2,000 pulses may be applied. However, either or both of the values for maximum energy density and pulses applied may vary. Also, since the male urethra is not approached axially, but rather laterally, the probe 30 needs to be repositioned once or twice, or possibly even thrice along the perineum 302 (in a direction extending from the scrotum 306 to the anus 304 or vice versa), as only a portion of the male urethra will be treated with each application of shockwaves. Further in this regard, it may be beneficial to use a focused probe, wherein a lens or other focusing element is used to focus the energy field at the depth of the male urethra when shock waves are applied perineally. For example, at the target location, the focused energy field may have an energy density of 0.05 to 0.08 mJ/mm$^2$ and this energy may be applied to the male urethra in pulses at a frequency of 2 Hz to 10 Hz, preferably 3 Hz to 5 Hz, for a total application of about 2,000 pulses.

Figure 13:
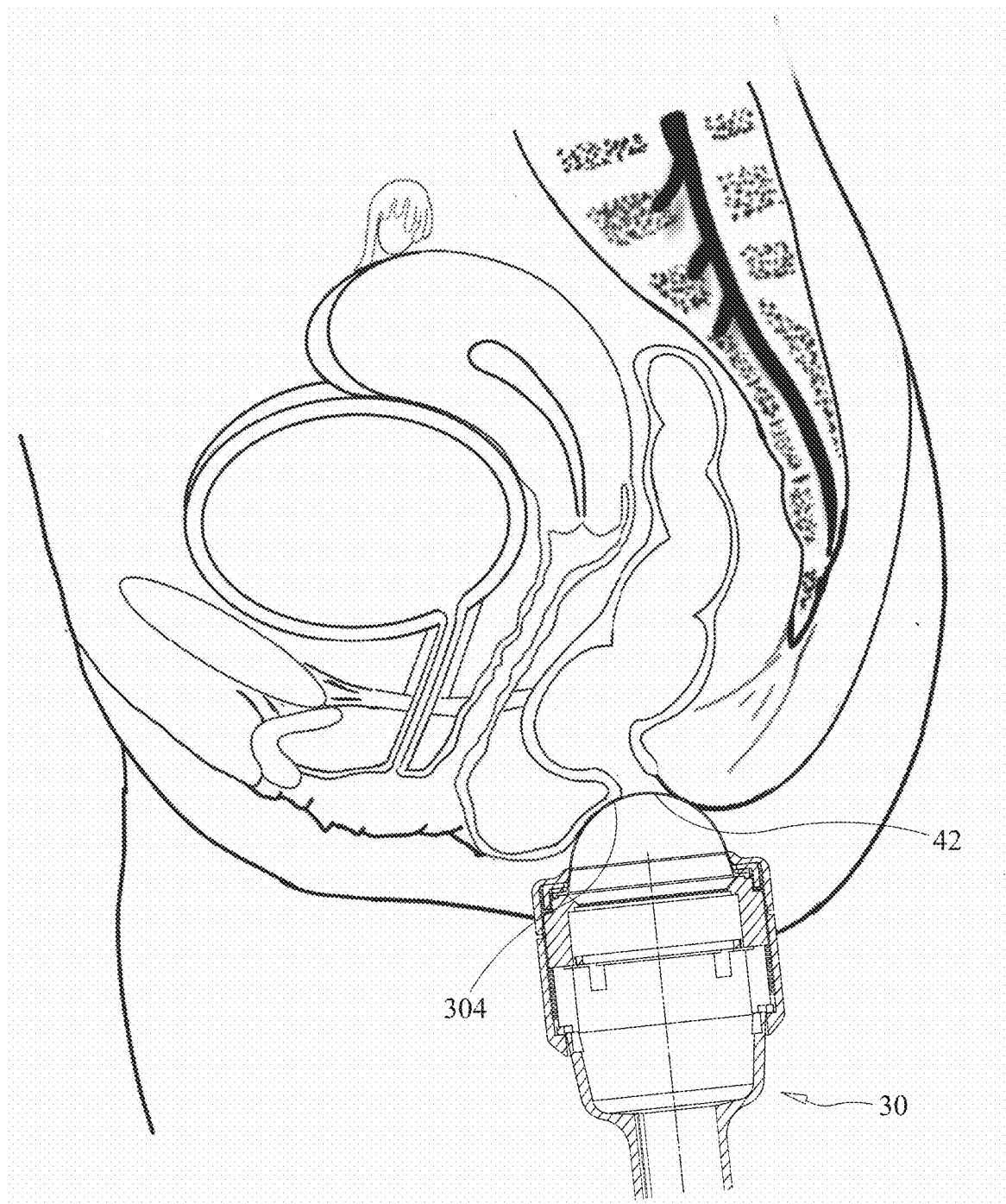
FIG. 13 illustrates contacting the flexible diaphragm of a probe to the anus of a female patient for treatment of the anal sphincter and/or rectum, according to an embodiment of the present invention.

In another embodiment, the present invention can be applied to treat the anal sphincter (anus) 304 and/or rectum of either a male or female patient. FIG. 13 illustrates contacting the flexible diaphragm 42 of probe 30 to the anus 304 of a female patient (although this could alternatively be done in the same manner to a male patient, see FIG. 14) for treatment of the anal sphincter and/or rectum. Application of a LEAP from probe 30 will encompass at least 50%, 60%, 70%, 80%, 90%, 95%, or preferably all of the volume of the inner anal sphincter with a cylinder of energy having characteristics described in previous embodiments herein. In this case the anus/anal sphincter is very close to the flexible diaphragm and therefore therapeutic ranges as low or lower than those used for axial treatment of the female urethra can be applied. However, higher therapeutic ranges can also be applied as the tissues involved in this treatment are less sensitive than those being treated during treatment of the female urethra. Accordingly, the 100% EFD value for these anal sphincter treatments described are preferably in the range of 0.01 mJ/mm$^2$ to 0.175 mJ/mm$^2$ or any subrange within this range, more preferably 0.05 mJ/mm$^2$ to 0.123 mJ/mm$^2$, or 0.05 mJ/mm$^2$ to 0.088 mJ/mm$^2$, or 0.05 mJ/mm$^2$ to 0.07 mJ/mm². Treatment of the inner anal sphincter as described may also require a number of applications of LEAPs (in the range from about 1,500 pulses to about 3,000 pulses for one treatment visit, preferably from 2,000 to 2,500 pulses. The frequency of application of the pulses may be in a range from about 2 Hz to 7 Hz, preferably in the range of about 3 Hz to 5 Hz.

Figure 14:
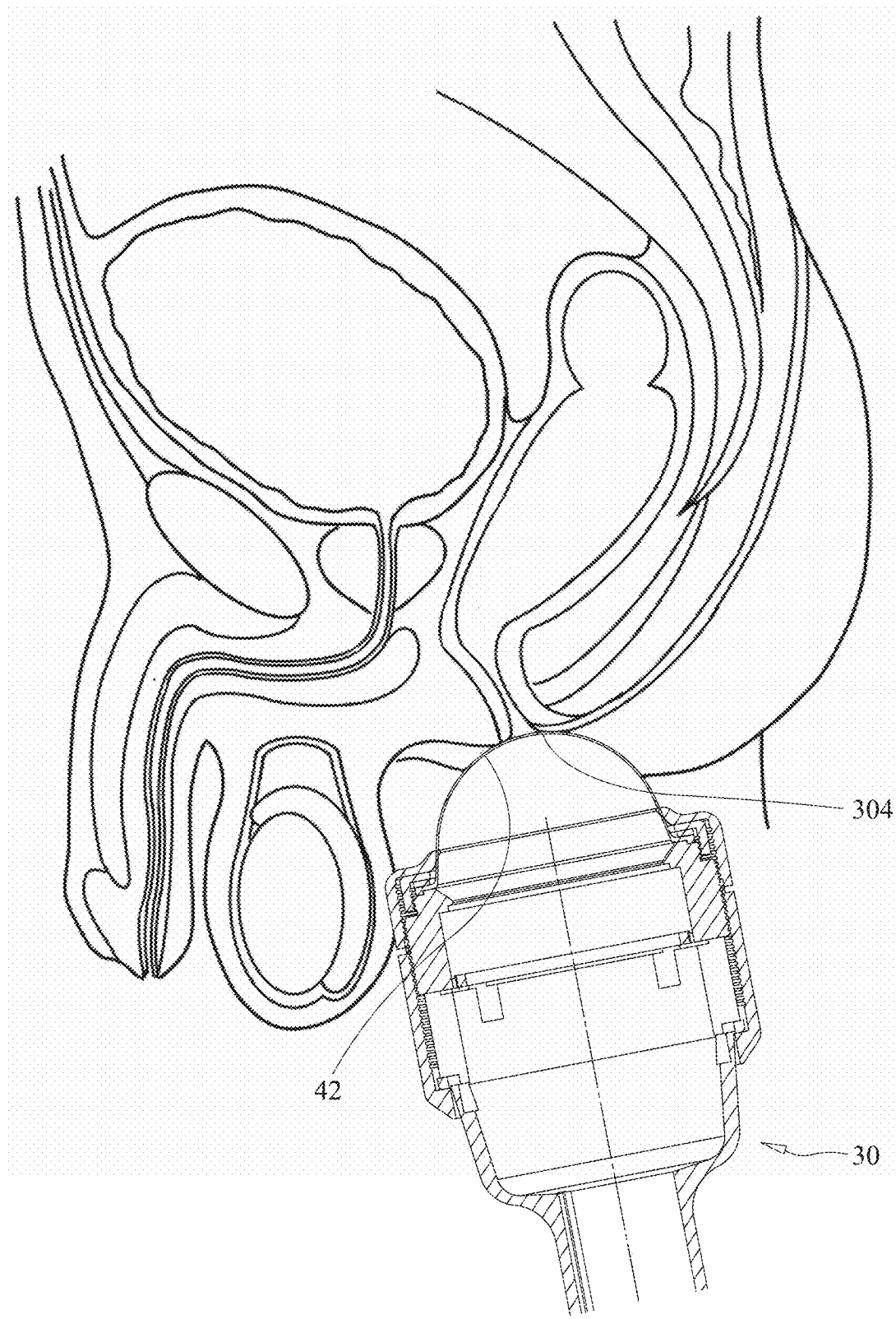
FIG. 14 illustrates contacting the flexible diaphragm of a probe to the anus of a male patient for treatment of the anal sphincter and/or rectum, according to an embodiment of the present invention.

In both of the embodiments of FIGS. 13-14, the target tissue being treated by a LEAP is therapeutically encompassed by a cylinder having energy density characteristics of those described previously with regard to the embodiments for axial treatment of the female urethra. Alternatively, the energy density characteristics may vary from those described with regard to those described for axial treatment of the urethra.

All of the embodiments described herein can be used as described to restore or improve functionality of tissues being treated, to facilitate generation of tissue and or improve vascularization of existing tissue. All embodiments may be used in combination with stem cell therapies as well for regeneration of tissue and vascularization.

EXAMPLE

Ten women with SUI were treated with an embodiment of the device in a manner as shown and described with regard to FIG. 4C. The average age of the subjects was 57. Their average urine leakage immediately prior to treatment was 44 g as measured by the standard 24-Hr. Pad Test. Each subject received ten applications of LEAPs over a six-week period. Each application consisted of 2,500 pulses, half at 3 Hz and half at 5 Hz. The EFD at location 42D was 0.035 mJ/mm² and the minimum energy density was 0.018 mJ/mm² in a cylinder 80 with diameter 16 mm and length 4 cm. After the 10$^{th}$ application, the average urine leakage was 10 g, an improvement of 77%. This significantly exceeds the effectiveness of all known non-invasive treatments for SUI and compares favorably with surgical intervention. No side effects were observed.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of treating a urethra of a female patient, said method comprising:
providing an acoustic energy pulse generating apparatus;
contacting the acoustic energy pulse generating apparatus to a body of the patient, in contact with or adjacent to an end of the urethra;
generating an acoustic energy pulse and delivering the acoustic energy pulse into the body, in a direction along a length of the urethra; and
as a result of said providing, contacting, generating and delivering, reducing urinary incontinence.

2. The method of claim 1, wherein said delivering the acoustic energy pulse into the body is delivered only by said delivering in said direction along the length of the urethra, by said acoustic energy pulse generating apparatus in contact with or adjacent to the end of the urethra.

3. The method of claim 1, wherein said generating and delivering steps are performed multiple times.

4. The method of claim 3, wherein said generating and delivering steps are repeated for a period in the range of 2 to 20 minutes.

5. The method of claim 1, wherein said generating and delivering are repeated at a frequency in the range of 1 Hz to 10 Hz.

6. The method of claim 5, wherein said generating and delivering steps are repeated for a period in the range of 2 to 20 minutes.

7. The method of claim 6, wherein said method is performed multiple times on the patient, during each of a multiple number of visits spread out over a time period.

8. The method of claim 7, wherein the time period is a six week period.

9. The method of claim 1, wherein the acoustic energy pulse has a field with maximum energy density in the range of 0.005 to 0.123 mJ/mm².

10. An apparatus for generating acoustic energy pulses for delivery into a living body, said apparatus comprising
a housing comprising an opening and a longitudinal axis, wherein said longitudinal axis extends through said opening;
an acoustic energy pulse generator wherein at least a portion of said acoustic energy pulse generator is contained within said housing; and
a contact portion configured to be placed in contact with or adjacent to the living body, and positioned such that an acoustic energy pulse generated by said acoustic energy pulse generator passes through said contact portion;
wherein said acoustic energy pulse generator is configured to generate and deliver the acoustic energy pulse along a female urethra of the living body in a direction along a length of the female urethra, said acoustic energy pulse having an energy density field that is configured for treating the female urethra and, as a result of said treating, reducing urinary incontinence; and
wherein a minimum energy density of a first volume of said energy density field is at least 50% of a maximum energy density of said energy density field and said first volume is configured to encompass a second volume of at least thirty percent of urethral sphincter muscles of the female urethra.

11. The apparatus of claim 10, wherein said acoustic energy pulse generator comprises a driver having a largest dimension in a range of 4.0 cm to 8.5 cm.

12. The apparatus of claim 11, wherein said driver is made of aluminum.

13. The apparatus of claim 12, wherein said aluminum is aircraft grade aluminum.

14. The apparatus of claim 13, wherein said aircraft grade aluminum comprises 7075 T6 aluminum.

15. The apparatus of claim 11, wherein said acoustic energy pulse generator comprises a coil, said apparatus further comprising a resilient member retaining said driver in a position relative to said coil.

16. The apparatus of claim 10, wherein said acoustic energy pulse generator comprises a coil, a driver and a resilient member retaining said driver in a position relative to said coil; wherein at least one side of said driver is covered by a coating.

17. The apparatus of claim 16, wherein said coating is configured to prevent or lessen cavitation erosion of said driver that can occur with repeated generations and deliveries of said acoustic energy pulses.

18. The apparatus of claim 16, wherein said coating completely covers at least a side of said driver opposite the coil.

19. The apparatus of claim 10, further comprising a stabilizing system comprising a stabilizing mechanism configured to maintain said contact portion in contact with the living body under a constant amount of force.

20. The apparatus of claim 19, wherein said stabilizing system is configured to maintain said contact portion in a stable position relative to the living body during a procedure.

21. The apparatus of claim 19, wherein said stabilizing system comprises an adjustable arm configured to allow said housing to be attached thereto.

22. The apparatus of claim 19, wherein said stabilizing mechanism comprises a base, a movable member and a biasing member; wherein said movable member is configured to move relative to said base and said biasing member is configured to apply a counterforce to said movable member when said movable member is driven against said biasing member.

23. The apparatus of claim 22, wherein movement of said movable member relative to said base moves and/or adjusts a force applied by said contact portion.

24. The apparatus of claim 19, wherein said stabilizing system is configured to maintain said contact portion in contact with the urethra of the living body in a relatively fixed position during an entirety of a procedure performed on the living body.

25. An apparatus for generating acoustic energy pulses for delivery into a living body for treatment of a urethra of a female patient, said apparatus comprising a housing comprising an opening and a longitudinal axis, wherein said longitudinal axis extends through said opening;
  an acoustic energy pulse generator wherein at least a portion of said acoustic energy pulse generator is contained within said housing;
  a contact portion configured to be placed in contact with or adjacent to the urethra, and positioned such that an acoustic energy pulse generated by said acoustic energy pulse generator passes through said contact portion and along a length of the urethra; and
  a stabilizing system comprising a stabilizing mechanism configured to maintain said contact portion in contact with the living body under a constant amount of force.

26. The apparatus of claim 25, wherein said constant amount of force is an amount in a range from 0.1 to 5 pounds force (lbf).

27. The apparatus of claim 25, wherein said constant amount of force is an amount in a range from 0.5 to 3 pounds force (lbf).

28. The apparatus of claim 25, wherein a maximum dimension of said housing in a direction orthogonal to said longitudinal axis is less than or equal to 140 mm.

29. The apparatus of claim 28, wherein said maximum dimension of said housing in a direction orthogonal to said longitudinal axis is less than or equal to 125 mm.

30. The apparatus of claim 29, wherein said maximum dimension of said housing in a direction orthogonal to said longitudinal axis is in a range from 70 mm to 90 mm.

31. A method of treating an anus of a patient, said method comprising:
  providing an acoustic energy pulse generating apparatus;
  contacting the acoustic energy pulse generating apparatus to a body of the patient, in contact with or adjacent to the anus of the patient; and
  generating an acoustic energy pulse and delivering the acoustic energy pulse into the body;
  wherein at least a portion of an anal sphincter or a rectum of the patient is encompassed by the acoustic energy pulse to restore or improve functionality of the anal sphincter and/or rectum, to facilitate generation of tissue of the anal sphincter and/or rectum, and/or to improve vascularization of the anal sphincter and/or rectum.

32. The method of claim 31, wherein the acoustic energy pulse is provided to have an energy flux density (EFD) in a predetermined therapeutic range where applied to the at least a portion of an anal sphincter or rectum.

33. The method of claim 32, wherein a maximum of the EFD is in the range from 0.01 mJ/mm$^2$ to 0.175 mJ/mm$^2$.

34. The method of claim 32, wherein a maximum of the EFD is in the range from 0.05 mJ/mm$^2$ to 0.123 mJ/mm$^2$.

35. The method of claim 32, wherein a maximum of the EFD is in the range from 0.05 mJ/mm$^2$ to 0.088 mJ/mm$^2$.

36. The method of claim 32, wherein a maximum of the EFD is in the range from 0.05 mJ/mm$^2$ to 0.07 mJ/mm$^2$.

37. The method of claim 32, wherein the EFD in the predetermined therapeutic range can be measured at all points within a space in a shape of an imaginary cylinder that encompasses the at least a portion of the anal sphincter or the rectum; and
  wherein a minimum energy density for said pulse at all locations within said cylindrically shaped space is at least 50% of a maximum energy density for said pulse within said space.

38. The method of claim 37, wherein the imaginary cylinder has a diameter in the range from 10 mm to 18 mm.

39. The method of claim 32, wherein at least 50% of the anal sphincter is encompassed by the EFD in the predetermined therapeutic range.

40. The method of claim 31, wherein said generating and delivering steps are performed multiple times.

41. The method of claim 40, wherein a number of said multiple times which said generating and delivering steps are repeated in the range from 1,500 to 3,000.

42. The method of claim 41 wherein said generating and delivering steps are repeated in the range from 1,500 to 3,000 times for one treatment visit.

43. The method of claim 40, wherein a number of said multiple times which said generating and delivering steps are repeated in the range from 2,000 to 2,500.

44. The method of claim 40, wherein said delivering steps are applied at a frequency in the range from 2 Hz to 7 Hz.

45. The method of claim 44, wherein said delivering steps are applied at a frequency in the range from 3 Hz to 5 Hz.

46. An apparatus for generating acoustic energy pulses for delivery into a living body, said apparatus comprising
  a housing comprising an opening and a longitudinal axis, wherein said longitudinal axis extends through said opening;
  an acoustic energy pulse generator wherein at least a portion of said acoustic energy pulse generator is contained within said housing; and
  a contact portion configured to be placed in contact with or adjacent to the living body, and positioned such that an acoustic energy pulse generated by said acoustic energy pulse generator passes through said contact portion;
  wherein said acoustic energy pulse generator is configured to generate and deliver the acoustic energy pulse to encompass at least a portion of an anal sphincter or a rectum of the living body to restore or improve functionality of the anal sphincter and/or rectum, to facilitate generation of tissue of the anal sphincter and/or rectum, and/or to improve vascularization of the anal sphincter and/or rectum;

wherein the acoustic energy pulse is provided to have an energy flux density (EFD) in a predetermined therapeutic range where encompassing the at least a portion of the anal sphincter or rectum; and wherein said acoustic energy pulse generator is configured to generate and deliver the acoustic energy pulse to encompass at least 50% of an inner anal sphincter of the anal sphincter with the EFD in the predetermined therapeutic range.

47. The apparatus of claim 46, wherein the EFD in the predetermined therapeutic range can be measured at all points within a space in the shape of an imaginary cylinder that encompasses the at least a portion of the anal sphincter, inner anal sphincter or the rectum; and wherein a minimum energy density for said pulse at all locations within said cylindrically shaped space is at least 50% of a maximum energy density for said pulse within said space.

48. An apparatus for generating acoustic energy pulses for delivery into a living body, said apparatus comprising a housing comprising an opening and a longitudinal axis, wherein said longitudinal axis extends through said opening;

an acoustic energy pulse generator wherein at least a portion of said acoustic energy pulse generator is contained within said housing; and a contact portion configured to be placed in contact with or adjacent to the living body, and positioned such that an acoustic energy pulse generated by said acoustic energy pulse generator passes through said contact portion;

wherein said acoustic energy pulse generator is configured to generate and deliver the acoustic energy pulse to encompass at least a portion of an anal sphincter, inner anal sphincter or a rectum of the living body to restore or improve functionality of the anal sphincter and/or inner anal sphincter and/or rectum, to facilitate generation of tissue of the anal sphincter and/or inner anal sphincter and/or rectum, and/or to improve vascularization of the anal sphincter and/or inner anal sphincter and/or rectum;

wherein the acoustic energy pulse is provided to have an energy flux density (EFD) in a predetermined therapeutic range where encompassing the at least a portion of the anal sphincter and/or inner anal sphincter and/or rectum;

wherein the EFD in the predetermined therapeutic range can be measured at all points within a space in a shape of an imaginary cylinder that encompasses the at least a portion of the anal sphincter and/or inner anal sphincter and/or rectum; and wherein a minimum energy density for said pulse at all locations within said cylindrically shaped space is at least 50% of a maximum energy density for said pulse within said space.

49. The apparatus of claim 48, wherein said acoustic energy pulse generator is configured to generate and deliver the acoustic energy pulse to encompass at least 50% of the inner anal sphincter with the EFD in the predetermined therapeutic range.

* * * * *